United States Patent
Gunderson et al.

(10) Patent No.: US 8,798,750 B2
(45) Date of Patent: Aug. 5, 2014

(54) IDENTIFYING A LEAD RELATED CONDITION BASED ON DETECTING NOISE SUBSEQUENT TO SIGNAL DELIVERY

(75) Inventors: Bruce D. Gunderson, Plymouth, MN (US); Kevin A. Wanasek, Princeton, MN (US); Charles D. Swerdlow, Los Angeles, CA (US)

(73) Assignee: Medtronic, Inc., Minneapolis, MN (US)

( * ) Notice: Subject to any disclaimer, the term of this patent is extended or adjusted under 35 U.S.C. 154(b) by 615 days.

(21) Appl. No.: 12/719,650

(22) Filed: Mar. 8, 2010

(65) Prior Publication Data

US 2011/0054558 A1 Mar. 3, 2011

Related U.S. Application Data

(60) Provisional application No. 61/237,154, filed on Aug. 26, 2009, provisional application No. 61/285,459, filed on Dec. 10, 2009.

(51) Int. Cl.
*A61N 1/08* (2006.01)
*A61B 5/0424* (2006.01)
*A61N 1/37* (2006.01)
*A61B 5/00* (2006.01)

(52) U.S. Cl.
CPC . *A61N 1/08* (2013.01); *A61N 1/371* (2013.01); *A61N 2001/083* (2013.01); *A61B 5/7203* (2013.01); *A61B 5/7217* (2013.01); *A61B 5/0424* (2013.01)
USPC ........ 607/27; 607/9; 607/29; 607/36; 607/37; 607/38; 607/115

(58) Field of Classification Search
CPC .............. A61N 1/3704; A61N 1/3702; A61N 1/36135; A61N 1/365; A61N 1/08; A61N 1/37; A61N 1/371; A61N 1/3712; A61N 1/37252; A61N 2001/083; A61N 1/04; A61N 1/0408; A61N 1/0472; A61N 1/36146; A61N 1/36514; A61B 5/7203; A61B 5/0031; A61B 5/7217; A61B 5/0006; A61B 5/0538; A61B 5/04012; A61B 5/0402; A61B 5/042; A61B 5/0424; A61B 5/6869; A61B 2562/0209; A61B 5/0205; A61B 5/04004; A61B 5/0422; A61B 5/0428; A61B 5/0478; A61M 2230/00; G06F 19/3406
USPC .............. 607/1–2, 9, 27, 29, 36–38, 115, 119
See application file for complete search history.

(56) References Cited

U.S. PATENT DOCUMENTS 4,374,382 A 2/1983 Markowitz
5,117,824 A 6/1992 Keimel et al.
(Continued)

OTHER PUBLICATIONS

International Preliminary Report on Patentability from corresponding PCT Application Serial No. PCT/US2010/043549 dated Dec. 16, 2011 (16 pages).

(Continued)

*Primary Examiner* — Deborah Malamud
(74) *Attorney, Agent, or Firm* — Michael J. Ostrom; Stephen W. Bauer

(57) ABSTRACT

In general, the disclosure describes techniques for detecting lead related conditions, such as lead fractures or other lead integrity issues. As described herein, delivering an electrical signal through selected electrodes may result in, reveal, or amplify noise if a lead related condition is present. A processor may detect electrical noise indicative of the lead related condition subsequent to the delivery of the electrical signal, and identify a lead related condition in response to detecting the noise.

34 Claims, 16 Drawing Sheets

(56) References Cited

U.S. PATENT DOCUMENTS

| | | |
|---|---|---|
| 5,545,186 A | 8/1996 | Olson et al. |
| 5,755,736 A | 5/1998 | Gillberg et al. |
| 5,776,168 A | 7/1998 | Gunderson |
| 6,741,886 B2 * | 5/2004 | Yonce .................... 600/510 |
| 7,047,083 B2 | 5/2006 | Gunderson et al. |
| 7,146,211 B2 * | 12/2006 | Frei et al. .................. 607/2 |
| 7,236,828 B2 | 6/2007 | Casavant et al. |
| 7,289,851 B2 | 10/2007 | Gunderson et al. |
| 7,333,855 B2 | 2/2008 | Gunderson et al. |
| 7,369,893 B2 | 5/2008 | Gunderson |
| 7,539,540 B2 | 5/2009 | Gunderson et al. |
| 7,567,835 B2 | 7/2009 | Gunderson et al. |
| 2005/0137636 A1 | 6/2005 | Gunderson et al. |
| 2008/0161870 A1 | 7/2008 | Gunderson |
| 2008/0215110 A1 | 9/2008 | Gunderson |
| 2009/0299201 A1 | 12/2009 | Gunderson |
| 2010/0023084 A1 | 1/2010 | Gunderson |

OTHER PUBLICATIONS

Reply to Written Opinion dated Oct. 26, 2010, from international application No. PCT/US2010/043549, filed Nov. 23, 2011, 11 pp.

Reply to Written Opinion from corresponding PCT Application Serial No. PCT/US2010/043549 filed Feb. 14, 2011 (12 pages).

Eugene H. Chung, M.D. et al., "Analysis of Pacing/Defibrillator Lead Failure Using Device Diagnostics and Pacing Maneuvers", PACE, vol. 32 (Apr. 2009) pp. 547-549.

Written Opinion from corresponding PCT Application Serial No. PCT/US2010/043549 dated Oct. 26, 2011 (7 pages).

International Search Report and Written Opinion from corresponding PCT Application Serial No. PCT/US2010/043549 dated Oct. 12, 2010 (14 pages).

* cited by examiner

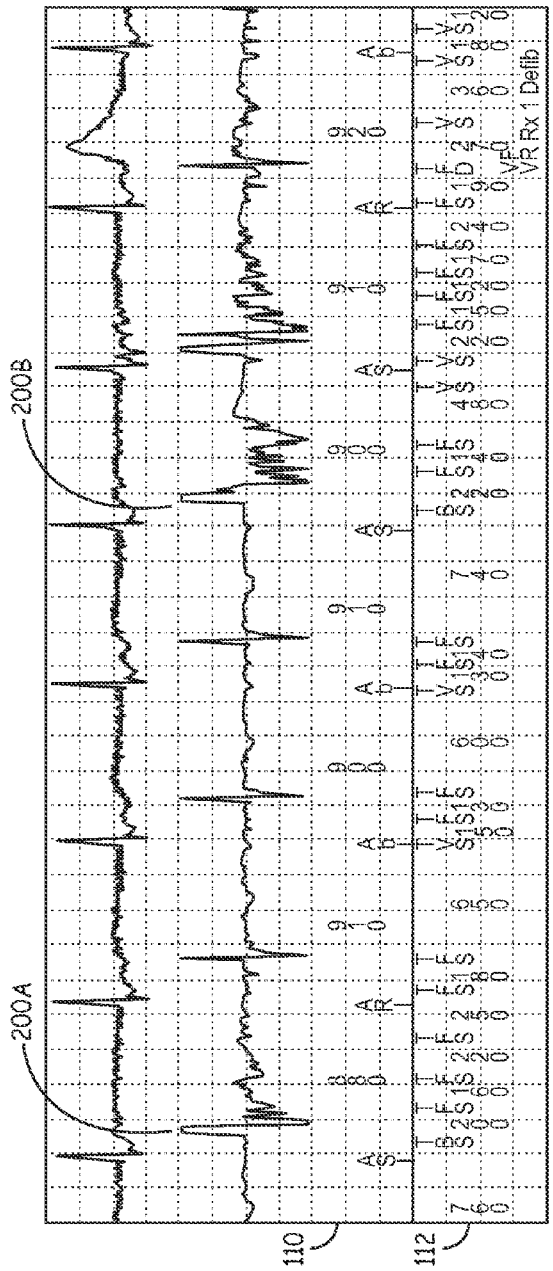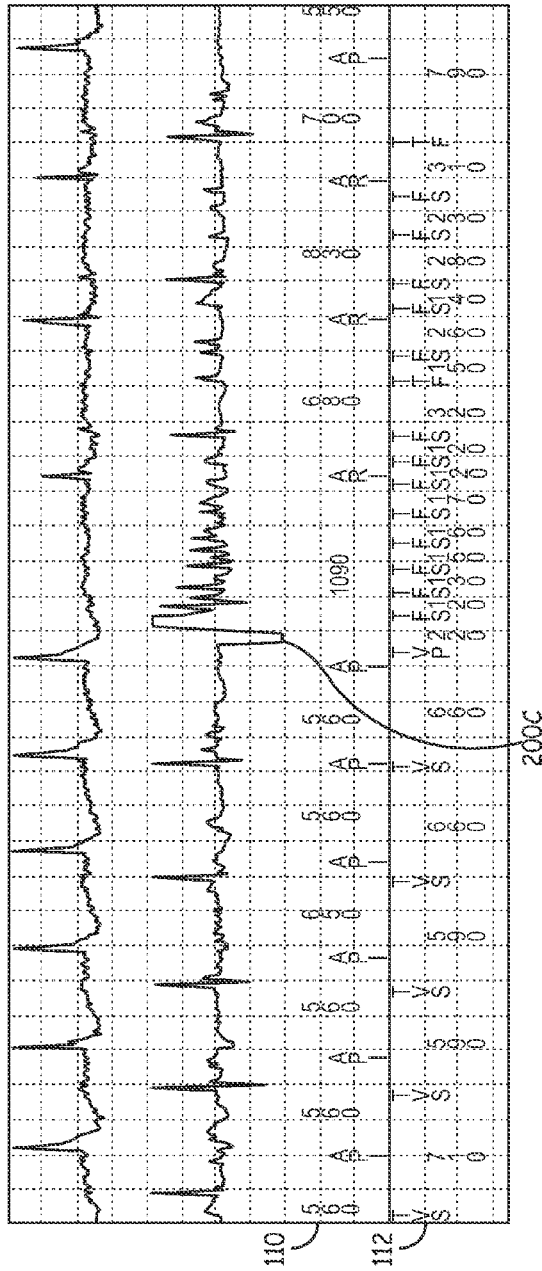

IDENTIFYING A LEAD RELATED CONDITION BASED ON DETECTING NOISE SUBSEQUENT TO SIGNAL DELIVERY

This application claims the benefit of U.S. Provisional Application Nos. 61/237,154, filed on Aug. 26, 2009, and 61/285,459, filed on Dec. 10, 2009, the entire contents of which are incorporated herein by reference.

TECHNICAL FIELD

The disclosure relates to medical devices and, more particularly, medical devices that are coupled to leads to sense electrical signals within a patient and/or deliver electrical signals to a patient.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissue. Some therapies include the delivery of electrical signals, e.g., stimulation, to such organs or tissues. Some medical devices may employ one or more elongated electrical leads carrying electrodes for the delivery of therapeutic electrical signals to such organs or tissues, electrodes for sensing intrinsic electrical signals within the patient, which may be generated by such organs or tissue, and/or other sensors for sensing physiological parameters of a patient.

Medical leads may be configured to allow electrodes or other sensors to be positioned at desired locations for delivery of therapeutic electrical signals or sensing. For example, electrodes or sensors may be carried at a distal portion of a lead. A proximal portion of the lead may be coupled to a medical device housing, which may contain circuitry such as signal generation and/or sensing circuitry. In some cases, the medical leads and the medical device housing are implantable within the patient. Medical devices with a housing configured for implantation within the patient may be referred to as implantable medical devices.

Implantable cardiac pacemakers or cardioverter-defibrillators, for example, provide therapeutic electrical signals to the heart via electrodes carried by one or more implantable medical leads. The therapeutic electrical signals may include pulses or shocks for pacing, cardioversion, or defibrillation. In some cases, a medical device may sense intrinsic depolarizations of the heart, and control delivery of therapeutic signals to the heart based on the sensed depolarizations. Upon detection of an abnormal rhythm, such as bradycardia, tachycardia or fibrillation, an appropriate therapeutic electrical signal or signals may be delivered to restore or maintain a more normal rhythm. For example, in some cases, an implantable medical device may deliver pacing stimulation to the heart of the patient upon detecting tachycardia or bradycardia, and deliver cardioversion or defibrillation shocks to the heart upon detecting fibrillation.

Implantable medical leads typically include a lead body containing one or more elongated electrical conductors that extend through the lead body from a connector assembly provided at a proximal lead end to one or more electrodes located at the distal lead end or elsewhere along the length of the lead body. The conductors connect signal generation and/or sensing circuitry within an associated implantable medical device housing to respective electrodes or sensors. Some electrodes may be used for both delivery of therapeutic signals and sensing. Each electrical conductor is typically electrically isolated from other electrical conductors and is encased within an outer sheath that electrically insulates the lead conductors from body tissue and fluids.

Medical lead bodies implanted for cardiac applications tend to be continuously flexed by the beating of the heart. Other stresses may be applied to the lead body, including the conductors therein, during implantation or lead repositioning. Patient movement can cause the route traversed by the lead body to be constricted or otherwise altered, causing stresses on the lead body and conductors. In rare instances, such stresses may fracture a conductor within the lead body. The fracture may be continuously present, or may intermittently manifest as the lead flexes and moves.

Additionally, the electrical connection between medical device connector elements and the lead connector elements can be intermittently or continuously disrupted. For example, connection mechanisms, such as set screws, may be insufficiently tightened at the time of implantation, followed by a gradual loosening of the connection. Also, lead pins may not be completely inserted.

Lead fracture, disrupted connections, or other causes of short circuits or open circuits may be referred to, in general, as lead related conditions. In the case of cardiac leads, sensing of an intrinsic heart rhythm through a lead can be altered by lead related conditions. Identifying lead related conditions may be challenging, particularly in a clinic, hospital or operating room setting, due to the often intermittent nature of lead related conditions. Identification of lead related conditions may allow modifications of the therapy or sensing, or lead replacement.

SUMMARY

In general, the disclosure describes techniques for identifying lead related conditions, such as lead fractures, or insufficient or intermittent coupling of a lead with a medical device. As described herein, the delivery of an electrical signal through a lead may result in, reveal, or amplify, noise indicative of a lead related condition if a lead related condition is present. Such noise may be detectable for a limited time after the delivery of the signal. Some example techniques for identifying lead related conditions include monitoring for such noise during a period that begins after the delivery of the signal and has a predetermined length. The example techniques include identifying a lead related condition utilizing a processor based on detecting such noise, e.g., detecting such noise due to, or based on, the amplification of such noise, subsequent to the delivery of the signal. The processor of the medical device may automatically identify the lead related condition based on noise detected subsequent to the delivery of the signal. In some examples, each of a plurality of electrical paths provided by one or more leads implanted in a patient are evaluated, e.g., by delivery of a signal via the path, and monitoring the path for subsequent noise indicative of a lead related condition.

In one example, a method comprises delivering an electrical signal via an electrical path that includes a medical lead, detecting noise indicative of a lead related condition on the electrical path within a period having a predetermined length subsequent to the delivery of the electrical signal, and identifying, by a processor, a lead related condition in response to detecting the noise indicative of the lead related condition.

In another example, a system comprises a signal generator that delivers an electrical signal via an electrical path that includes a medical lead, a sensing module that detects noise indicative of a lead related condition on the electrical path within a period having a predetermined length subsequent to the delivery of the electrical signal, and a processor that identifies a lead related condition in response to detecting the noise indicative of the lead related condition.

In another example, a system comprises means for delivering an electrical signal via an electrical path that includes a medical lead, means for detecting noise indicative of a lead related condition on the electrical path within a period having a predetermined length subsequent to the delivery of the electrical signal, and means for automatically identifying a lead related condition in response to detecting the noise indicative of the lead related condition.

In another example, a computer-readable medium comprises instructions for causing a programmable processor to deliver an electrical signal via an electrical path that includes a medical lead, detect noise indicative of a lead related condition on the electrical path within a period having a predetermined length subsequent to the delivery of the electrical signal, and identify a lead related condition in response to detecting the noise indicative of the lead related condition.

BRIEF DESCRIPTION OF DRAWINGS

FIGS. 16A and 16B illustrate example electrogram (EGM) signals that may indicate lead related conditions.

DETAILED DESCRIPTION

Figure 1:
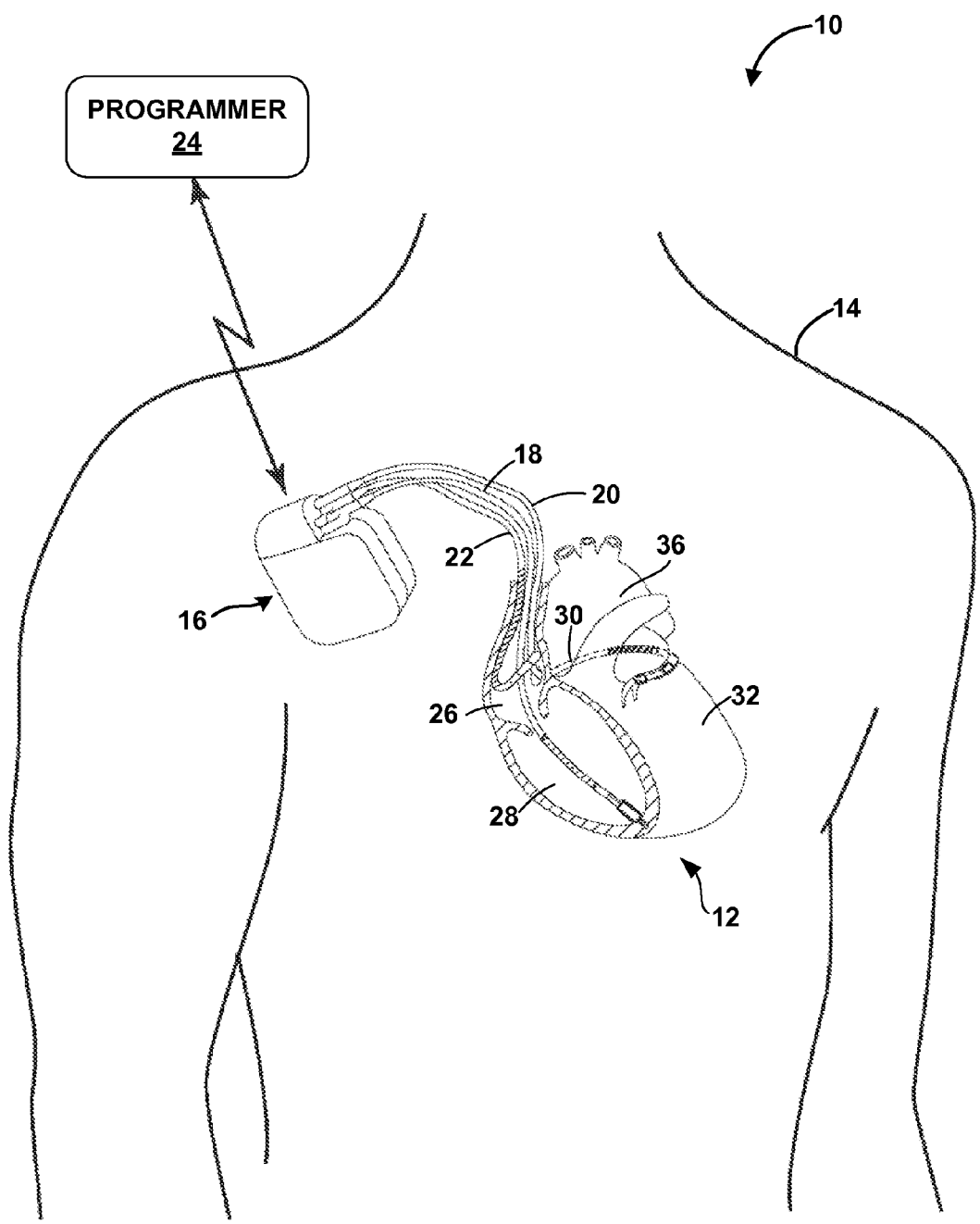
FIG. 1 is a conceptual drawing illustrating an example system that includes an implantable medical device (IMD) coupled to implantable medical leads.

FIG. 1 is a conceptual diagram illustrating an example system 10 that may be used for sensing of physiological parameters of patient 14 and/or to provide therapy to heart 12 of patient 14. System 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 12 is ordinarily, but not necessarily a human patient.

Although an implantable medical device and delivery of electrical signals to heart 12 are described herein as examples, the techniques for detecting lead related conditions of this disclosure may be applicable to other medical devices and/or other therapies. In general, the techniques described in this disclosure may be implemented by any medical device, e.g., implantable or external, that includes leads to sense electrical signals or other physiological parameters from a patient, and/or deliver electrical signals to a patient, or any one or more components of a system including such a medical device. As one alternative example, IMD 16 may be a neurostimulator that delivers electrical stimulation to and/or monitor conditions associated with the brain, spinal cord, or neural tissue of patient 16.

In the example of FIG. 1, leads 18, 20, 22 extend into the heart 12 of patient 16 to sense electrical activity of heart 12 and/or deliver electrical signals to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 10 may additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, system 10 may additionally or alternatively include temporary or permanent epicardial or subcutaneous leads, instead of or in addition to transvenous, intracardiac leads 18, 20 and 22. Such leads may be used for one or more of cardiac sensing, pacing, or cardioversion/defibrillation.

IMD 16 may sense electrical signals attendant to the depolarization and repolarization of heart 12 via electrodes (not shown in FIG. 1) coupled to at least one of the leads 18, 20, 22. In some examples, IMD 16 provides pacing stimulation to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., shocks with increasing energy levels, until a fibrillation of heart 12 is stopped. IMD 16 may detect fibrillation employing one or more fibrillation detection techniques known in the art.

In some examples, programmer 24 comprises a handheld computing device, computer workstation, or networked computing device. Programmer 24 may include a user interface that receives input from a user. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance.

As another example, the user may use programmer 24 to retrieve information from IMD 16 regarding the performance or integrity of IMD 16 or other components of system 10, such as leads 18, 20 and 22, or a power source of IMD 16. In some examples, this information may be presented to the user as an alert. For example, a lead related condition identified based on noise sensed subsequent to delivery of an electrical signal may trigger IMD 16 to transmit an alert to the user via programmer 24.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
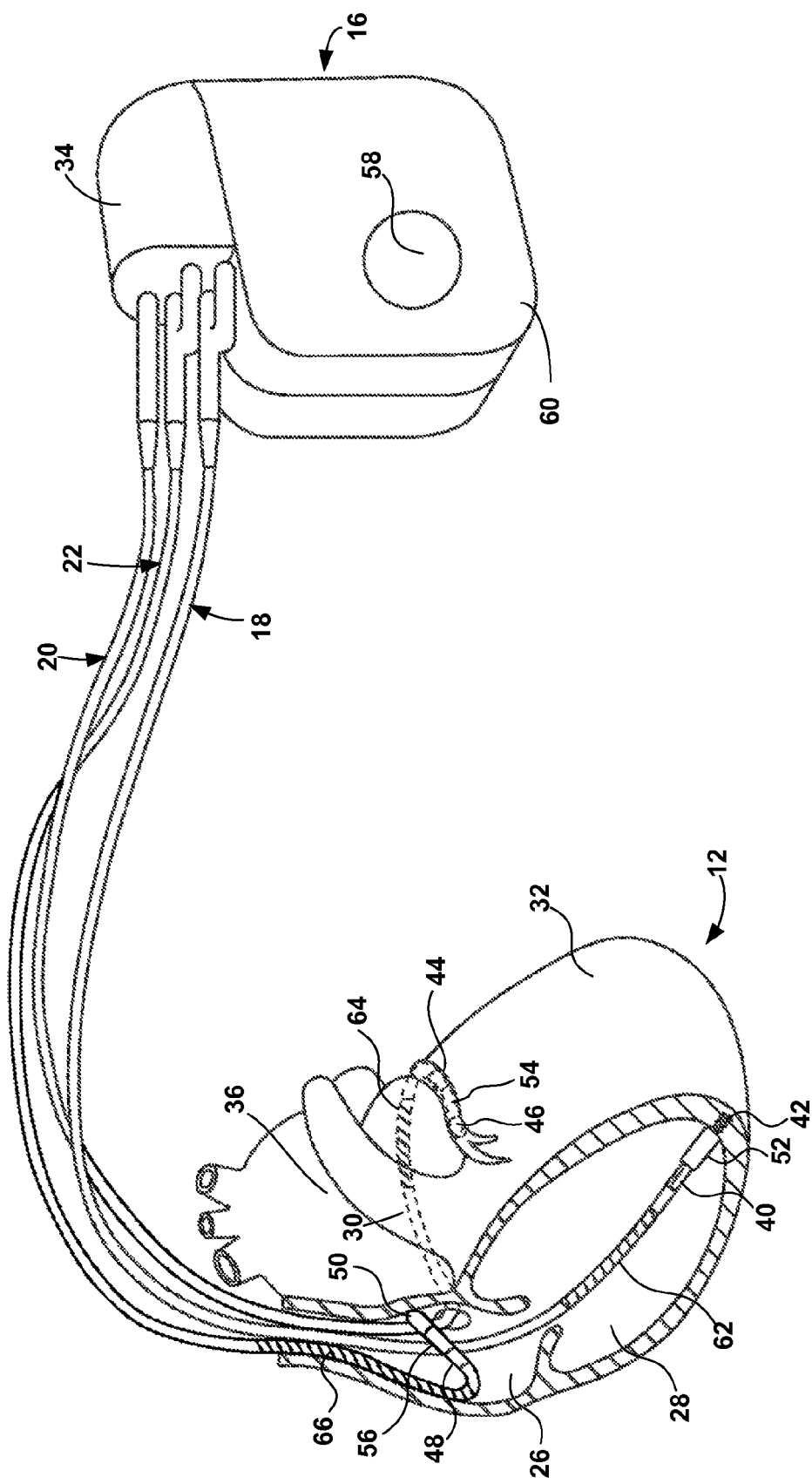
FIG. 2 is a conceptual drawing illustrating the example IMD and leads of FIG. 1 in conjunction with a heart.

FIG. 2 is a conceptual diagram illustrating IMD 16 and leads 18, 20 and 22 of system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic signals, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration.

In some examples, IMD 16 delivers pacing stimulation via bipolar combinations of electrodes 40, 42, 44, 46, 48 and 50 to produce depolarization of cardiac tissue of heart 12. In some examples, IMD 16 delivers pacing stimulation via any of electrodes 40, 42, 44, 46, 48 and 50 in combination with housing electrode 58 in a unipolar configuration. Furthermore, IMD 16 may deliver defibrillation shocks to heart 12 via any combination of elongated electrodes 62, 64, 66, and housing electrode 58. Electrodes 58, 62, 64, 66 may also be used to deliver cardioversion shocks to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of electrical signals or sensing, their associated conductors and connectors, and any tissue or fluid between the electrodes, may define an electrical path.

The configuration of system 10 illustrated in FIGS. 1 and 2 is merely one example. In other examples, a system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

Figure 3:
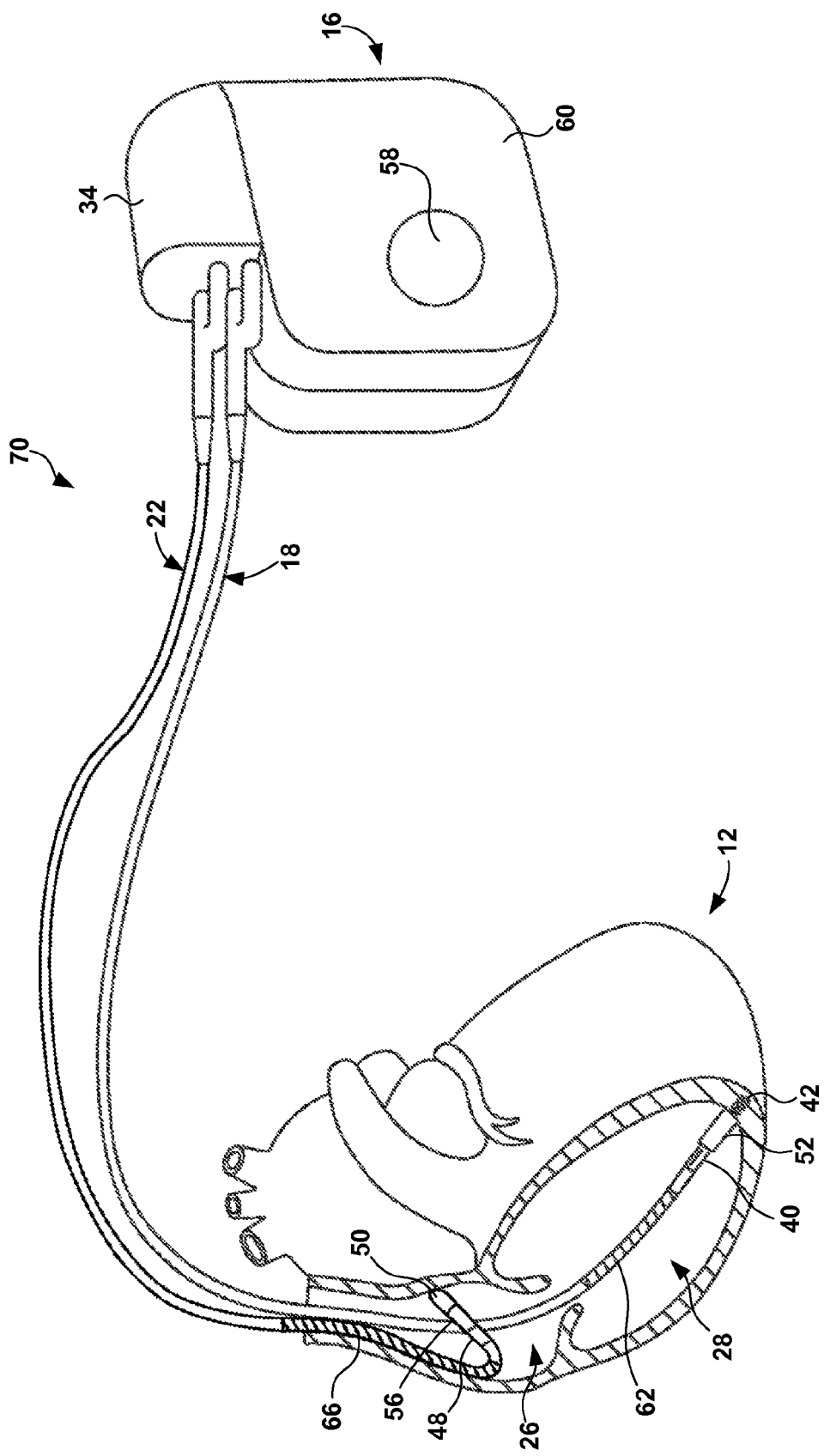
FIG. 3 is a conceptual drawing illustrating the example IMD of FIG. 1 coupled to a different configuration of implantable medical leads in conjunction with a heart.

In addition, in other examples, a system may include any suitable number of leads coupled to IMD 16, and each of the leads may extend to any location within or proximate to heart 12. For example, other examples of systems may include three transvenous leads located as illustrated in FIGS. 1 and 2, and an additional lead located within or proximate to left atrium 36. As another example, other examples of systems may include a single lead that extends from IMD 16 into right atrium 26 or right ventricle 28, or two leads that extend into a respective one of the right ventricle 26 and right atrium 26. An example of this type of system is shown in FIG. 3. Any electrodes located on these additional leads may be used in sensing and/or signal delivery configurations.

Additionally, as previously mentioned, IMD 16 need not deliver therapy to heart 12. In general, this disclosure may be applicable to any medical device, e.g., implantable or external, that includes leads to sense electrical signals or other physiological parameters from a patient, and/or deliver electrical signals to a patient.

FIG. 3 is a conceptual diagram illustrating another example of system 70, which is similar to system 10 of FIGS. 1 and 2, but includes two leads 18, 22, rather than three leads. Leads 18, 22 are implanted within right ventricle 28 and right atrium 26, respectively. System 70 shown in FIG. 3 may be useful for providing defibrillation shocks and pacing stimulation to heart 12. Detection of lead related conditions according to this disclosure may be performed in two lead systems in the manner described herein with respect to three lead systems.

Figure 4:
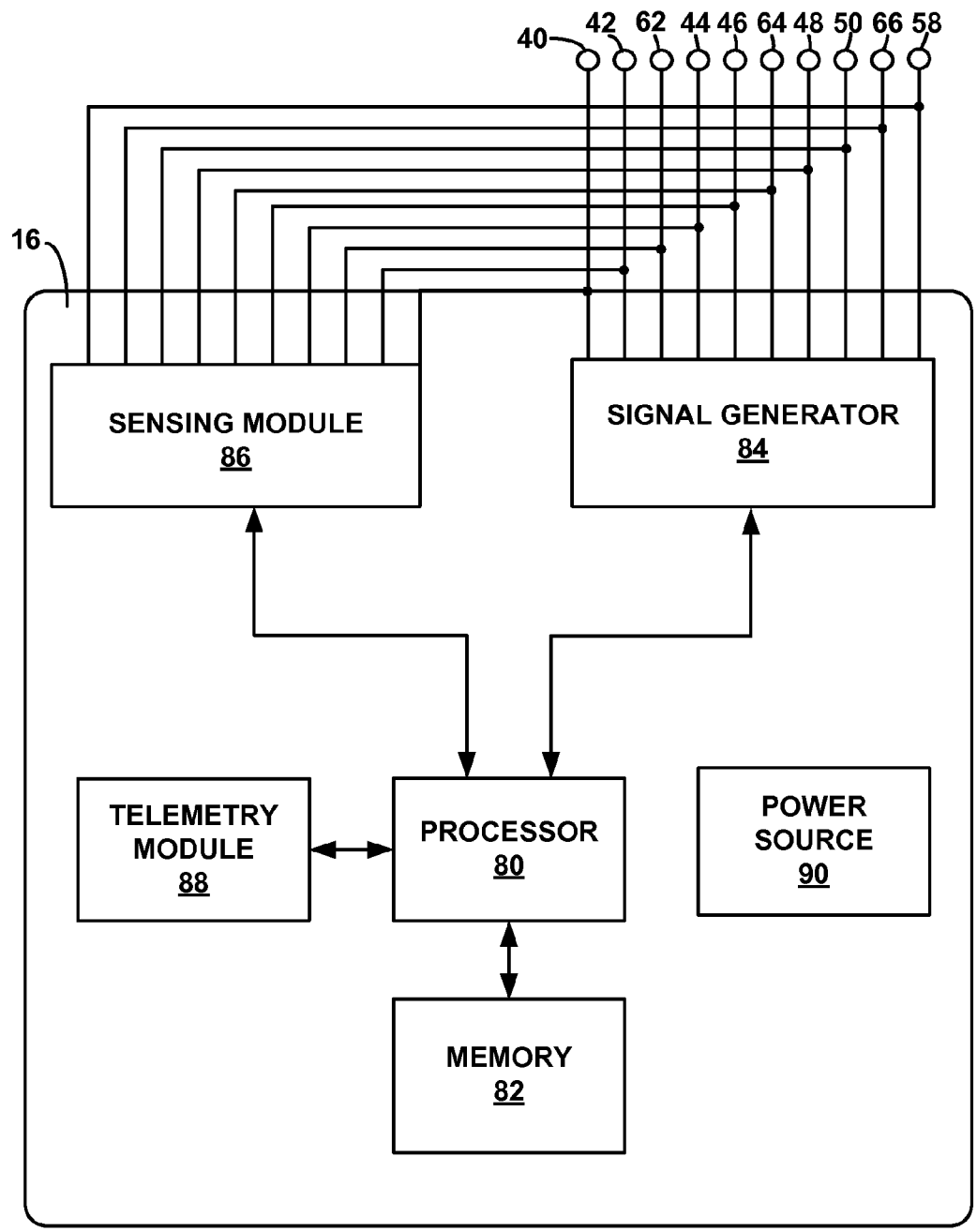
FIG. 4 is a functional block diagram illustrating an example configuration of the IMD of FIG. 1.

FIG. 4 is a functional block diagram illustrating an example configuration of IMD 16. In the illustrated example, IMD 16 includes a processor 80, memory 82, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver therapy to heart 12 according to a selected one or more of therapy programs, which may be stored in memory 82. For example, processor 80 may control stimulation generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver therapeutic electrical signals to heart 12. For example, signal generator 84 may deliver defibrillation shocks to heart 12 via at least two electrodes 58, 62, 64, 66. Signal generator 84 may deliver pacing stimulation via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation signals in the form of electrical pulses. In other examples, signal generator may deliver one or more of these types of therapeutic electrical signals, such as sine waves, square waves, or other substantially continuous time signals.

Signal generator 84 may include a switch module and processor 80 may use the switch module to select, e.g., via a data/address bus, which of the available electrodes are used to deliver defibrillation shocks or pacing stimulation. The switch module may include a switch array, switch matrix, multiplexer, or any other type of switching device suitable to selectively couple the therapeutic electrical signal to selected electrodes.

Electrical sensing module 86 monitors signals from at least one of electrodes 40, 42, 44, 46, 48, 50, 58, 62, 64 or 66 in order to monitor electrical activity of heart 12. Sensing module 86 may also include a switch module to select which of the available electrodes are used to sense the heart activity, depending upon which electrode combination is used in the current sensing configuration. In some examples, processor 80 may select the electrodes that function as sense electrodes, i.e., select the sensing configuration, via the switch module within sensing module 86. Processor 80 may control the functionality of sensing module 86 by providing signals via a data/address bus.

Sensing module 86 may include one or more detection channels, each of which may comprise an amplifier. The detection channels may be used to sense the cardiac signals. Some detection channels may detect events, such as R- or P-waves, and provide indications of the occurrences of such events to processor 80. One or more other detection channels may provide the signals to an analog-to-digital converter, for processing or analysis by processor 80. In response to the signals from processor 80, the switch module within sensing module 86 may couple selected electrodes to selected detection channels.

For example, sensing module 86 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 80 then uses that detection in measuring frequencies of the sensed events. Different narrow band channels of sensing module 86 may have distinct functions. For example, various narrow band channels may be used to sense either atrial or ventricular events.

In one example, at least one narrow band channel may include an R-wave amplifier that receives signals from the sensing configuration of electrodes 40 and 42, which are used for sensing and/or pacing in right ventricle 28 of heart 12. Another narrow band channel may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a wide band channel which may comprise an amplifier with a relatively wider pass band than the R-wave or P-wave amplifiers. Signals from the selected sensing electrodes that are selected for coupling to this wide-band amplifier may be converted to multi-bit digital signals by an analog-to-digital converter (ADC) provided by, for example, sensing module 86 or processor 80. In some examples, processor 80 may store the digitized versions of signals from the wide band channel in memory 82 as electrograms (EGMs).

In some examples, processor 80 may employ digital signal analysis techniques to characterize the digitized signals from the wide band channel to, for example detect and classify the patient's heart rhythm. Processor 80 may detect and classify the patient's heart rhythm by employing any of the numerous signal processing methodologies known in the art.

Processor 80 may maintain programmable interval counters. For example, if IMD 16 is configured to generate and deliver pacing stimulation to heart 12, processor 80 may maintain programmable counters which control the basic time intervals associated with various modes of pacing, including anti-tachycardia pacing (ATP) and pacing associated with cardiac resynchronization therapy (CRT). Intervals maintained by processor 80 for pacing may include atrial and ventricular pacing escape intervals, refractory periods during which sensed P-waves and R-waves are ineffective to restart timing of the escape intervals, and, in examples in which pacing stimulation comprises pulses, the pulse widths of the pacing pulses. As another example, processor 80 may define a blanking period, and provide signals to sensing module 86 to blank one or more channels, e.g., amplifiers, for a period during and after delivery of a therapeutic electrical signal to heart 12. The durations of these intervals may be determined by processor 80 in response to stored data in memory 82. Processor 80 may also determine the amplitude of the cardiac pacing stimulation.

In some examples, processor 80 resets interval counters upon sensing of R-waves and P-waves with detection channels of sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing stimulation to one of the chambers of heart 12. Processor 80 may reset the interval counters upon the generation of pacing stimulation by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect a suspected tachyarrhythmia event, such as ventricular fibrillation or ventricular tachycardia. In some examples, a portion of memory 82 may be configured as a plurality of recirculating buffers, capable of holding series of measured intervals, which may be analyzed by processor 80 to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

Processor 80 may also control signal generator 84 and sensing module 86 to identify lead related conditions. Detection of lead related conditions may prevent or end inappropriate detection of cardiac events. Rapid, intermittent fracture of one or more of leads 18, 20, 22 or disconnection of the lead from IMD 16 may be interpreted by the IMD 16 as a plurality of sensed cardiac events, e.g., R-waves, and result in inappropriate detection of a cardiac arrhythmia by IMD 16. More particularly, "make/break" events resulting from intermittent fracture or disconnection of a conductor within a lead that is electrically connected to an electrode used in an electrode combination for a current sensing configuration may introduce noise into the signal received by a sensing channel of sensing module 86 that is electrically coupled to the electrode combination, e.g., the signal that represents depolarization of heart 12. An amplifier of the sensing channel may interpret such noise as events, e.g., R-waves, and provide indications of the events to processor 80. The rate of sensed events when such noise is present may be similar to or greater than that for detection of a tachyarrhythmia, and processor 80 may detect a tachyarrhythmia based on the noise.

To identify lead related conditions, processor 80 may control signal generator 84 to deliver an electrical signal, e.g., a pacing stimulation, which may be in the form of one or more pulses, via an electrical path that includes a combination of one or more of the electrodes on one or more of leads 18, 20, 22. The electrical signal is configured to result in, reveal, or amplify electrical noise if a lead related condition, e.g., conductor or connector failure, or insulation breach, is present. If a lead related condition is present, the electrical signal may cause a build-up of capacitive charge, e.g., at the lead-tissue interface and/or at the location of the fracture point. In addition, the lead related condition may be intermittent. As one example, an intermittent lead fracture or disconnection may fluctuate between a completed connection and a broken connection. The intermittent nature of the lead integrity issue may be detectable as noise indicative of a lead related condition on electrical path when the capacitive charge is present on the electrical path.

Processor 80 may control sensing module 86 to sense for electrical noise indicative of a lead related condition subsequent to the delivery of the electrical signal. For example, sensing module 86 may sense an EGM signal using the electrode configuration used to deliver the electrical signal. As described in further detail below, processor 80 may identify a lead related condition based on the sensed signal, e.g., based on whether electrical noise indicative of a lead related condition is sensed. If processor 80 senses electrical noise indicative of a lead related condition, processor 80 may automatically identify a lead related condition.

In some examples, processor 80 may control signal generator 84 to produce an electrical signal specifically for integrity testing. In other examples, processor 80 prompts sensing module 86 to sense for electrical noise indicative of a lead related condition subsequent to the delivery of a pacing stimulus delivered for therapeutic purposes, e.g., a pacing pulse to treat bradycardia or an antitachycardia pacing pulse.

In this case, the integrity testing is performed using the pacing stimulation, e.g., pulse or pulses, delivered for therapeutic purposes, thus eliminating the need to provide separate electrical signals to the heart of the patient specifically for integrity testing.

In either case, processor 80 may select the signal parameter values used by signal generator 84 to test lead integrity. In some examples, processor 80 selects the signal parameter values for lead integrity testing based on the electrode configuration that signal generator 84 will be using to deliver the electrical signal. The stimulation parameter values may be based on the therapy typically delivered using the selected channel. For example, if signal generator 84 typically delivers pacing therapy via the electrode configuration selected for integrity testing, signal generator 84 may perform the integrity test using one or more electrical signals with the stimulation parameter values typical of pacing, whether or not the electrical signal is delivered to provide therapy.

As an alternative, signal generator 84 may deliver a non-therapeutic electrical signal to test lead integrity. For example, signal generator 84 may deliver signals that do not necessarily deliver stimulation therapy to heart 12, due to, for example, the amplitudes of such signals and/or the timing of delivery of such signals. For example, these signals may comprise sub-threshold amplitude signals, e.g., below a threshold necessary to capture or otherwise activate tissue, such as cardiac tissue. In some cases, electrical signals may be delivered during a refractory period, in which case they also may not stimulate heart 12. Signal generator 84 may deliver non-therapeutic electrical signals if the electrode configuration selected for integrity testing is not typically used for therapy delivery, e.g., is only used for sensing electrical signals of heart 12. Examples of non-therapeutic electrical signals include sub-threshold, refractory, post sensed depolarization and pre T-wave, and fusion beat signals.

In some examples, regardless of whether the electrical signal for lead integrity testing provides a therapeutic effect, the selected signal parameters may be configured to increase electrical noise due to lead related conditions. An increase in the capacitive charge built up at the lead-tissue interface and/or the location of the lead integrity issue may result in an increase in the amplitude of the electrical noise due to the lead related condition. Therefore, increasing the signal amplitude and/or duration, e.g., pulse width, may increase electrical noise if a lead related condition is present. In some examples, electrical signals delivered for lead integrity testing may be at a maximum amplitude and/or a maximum duration, e.g., pulse width, available from signal generator 84. Additionally, a biphasic electrical signal that includes two portions of opposite polarity may allow the capacitive charge built up due to a lead related condition to dissipate during the second phase. Therefore, suppressing the second phase of a biphasic signal may increase electrical noise if a lead related condition is present.

During lead integrity testing, processor 80 may modify one or more signal parameter values of a therapeutic electrical signal delivered by signal generator 84 to increase electrical noise due to lead related conditions. Processor 80 may also select stimulation parameter values for non-therapeutic signals delivered by signal generator 84 for lead integrity testing that maximize electrical noise due to lead related conditions while avoiding tissue capture. In some examples, memory 82 stores sets of parameter values associated with specified electrode combinations for electrical signals used for lead integrity testing for selection by processor 80.

As another example, processor 80 may control delivery of additional electrical signals during lead integrity testing. For example, processor 80 may control delivery of pacing stimulation using signal parameter values typically used for pacing and one or more non-therapeutic electrical signals, e.g., during the refractory period of heart 12. The one or more non-therapeutic electrical signals may be configured to amplify noise due to lead related conditions, e.g., using an increased amplitude, increased duration or pulse width, and/or a signal with a single polarity. A signal with a single polarity may be achieved by use of a DC bias or suppression of a second phase of a biphasic pulse, as examples.

In some examples, the one or more additional signals delivered during the refractory period are additional pacing stimuli, e.g., pulses, with parameters values typically used for pacing, and may further be pacing stimuli having the same parameters as the therapeutic pacing stimulus. Thus, in some examples, a pacing pulse delivered for therapeutic purposes may be followed by delivery of one or more additional pacing pulses during the refractory period after the pacing pulse to amplify the noise indicative of a lead related condition. In some examples, signals such as pacing pulses are similarly delivered during the refractory period after an intrinsic depolarization of heart 12.

Processor 80 may perform lead integrity testing automatically, e.g., periodically according to a schedule, or in response to a command received via programmer 24. Processor 80 may test a variety of electrical paths that include two or more of electrodes 40, 42, 44, 46, 48, 50, 58, 62, 64 and 66. If an integrity issue is detected along one electrical path, processor 80 may test alternate electrode configurations to identify which conductor or connector of the path is experiencing an integrity issue. For example, if an integrity issue is detected when electrodes 40 and 42 are activated, processor 80 may test electrodes 40 and 42 independently, e.g., by separately testing each of 40 and 42 in combination with housing electrode 58, to determine which of electrodes 40 and 42, or its associated conductor(s) or connection(s), is causing the issue.

Processor 80 may control sensing module 86 to sense electrical noise subsequent to the delivery of an electrical signal for lead integrity testing. Sensing module 86 may sense electrical signals using each electrode configuration tested. Processor 80 may control detection or detect electrical noise using thresholds and/or digital signal processing. In some examples, processor 80 uses a shortened blanking period for sensing lead related noise. The blanking period may be configured to be long enough so that the electrical signal delivered for lead integrity testing is not sensed as a lead related condition. However, the blanking period used during lead integrity testing may not need to be long enough to prevent double counting of the R-wave of the cardiac cycle, as may be the case for a blanking period following delivery of a therapeutic electrical signal during periods in which lead integrity is not tested.

In some examples, processor 80 may identify each time the sensed signal exceeds a threshold value within a specified time interval or period having a predetermined length, e.g., of approximately 2 seconds, following the delivery of the electrical signal via signal generator 84. The interval or period may begin after a blanking period, which may be shortened, as discussed above. Processor 80 may count the number of times the sensed signal exceeds the threshold value.

In some examples, the threshold value may correspond to an intrinsic depolarization threshold, e.g., used to detect P-waves or R-waves. In some examples, processor 80 may determine the intervals between depolarizations sensed within the period subsequent to delivery of the electrical signal, during which sensed depolarizations may be the result of noise indicative of a lead related condition. Processor 80 may further determine the number of times the interval between these sensed depolarizations is less than a threshold time interval, e.g., a tachyarrhythmia time interval. The threshold time interval may be, as one example, approximately 200 milliseconds. Processor 80 may determine whether a lead related condition is present based on the number of times the sensed signal exceeds the threshold value and/or the number of tachyarrhythmia events detected within the specified time interval.

In some examples, IMD 16 may compare a signal detected after delivery of an electrical signal with a threshold value or baseline signal to detect noise indicative of a lead related condition. The comparison may be an analog comparison by a detection channel of sensing module 86 under the control of processor 80, or a digital comparison of a digitized EGM by processor 80. In the case of an analog comparison, sensing module 86 may include a channel that comprises an amplifier that provides a sensing threshold for sensing noise after delivery of an electrical signal. As discussed above, some channels provided by sensing module 86 may use automatically-adjusting sensitivity to detect heartbeats from sensed signals and avoid oversensing due to the T-wave of the cardiac cycle. However, in some examples, IMD 16 may use a fixed, high sensitivity channel or algorithm to detect lead related conditions. IMD 16 may detect low amplitude noise due to lead related conditions better using a fixed sensitivity instead of an automatically-adjusting sensitivity. In some examples, the signal is passed through a high pass filter prior to analysis by sensing module 86 or processor 80 to help prevent the sensing module or processor from interpreting T-waves as noise due to lead related conditions.

As another example, processor 80 may use digital signal processing techniques to determine whether a lead related condition is present. As one example, processor 80 may compare an EGM of an electrode combination being tested to a baseline EGM, which may correspond to a far-field EGM sensed at the same time as the EGM corresponding to the electrode configuration being tested. As another example, memory 82 may store a template EGM signal, and processor 80 may compare the sensed EGM signal to the template to determine whether electrical noise indicative of a lead related condition is present. For example, processor 80 may detect one or more wavelets in the sensed EGM corresponding to the electrode combination being tested that are not present in the far-field or template EGM signal and identify a lead related condition based on the detected wavelets. Processor 80 may perform the comparison during a specified time interval, e.g., of approximately 2 seconds, following the electrical signal delivered via signal generator 84 for integrity testing.

Sensing module 86 may include a detection channel configured to detect electrical noise due to lead related conditions. For example, sensing module 86 may include a channel without a low pass filter. A low pass filter may filter some of the electrical noise due to lead related conditions, so a detection channel without a low pass filter may improve the detection of lead related conditions. Additionally or alternatively, sensing module 86 may include a high pass filter. A high pas filter may filter T-waves of the cardiac cycle to help prevent processor 80 from interpreting the T-waves as noise due to lead related conditions. In examples in which sensing module 86 includes digital circuitry, the low pass filter may be switched off when sensing during lead integrity testing and/or the high pass filter may be switched on when sensing during lead integrity testing.

Processor 80 may automatically identify a lead related condition by determining whether a signal sensed subsequent to delivery of an electrical signal is indicative of a lead related condition, e.g., using any of the techniques described above. In addition, processor 80 may take one or more actions in response to detecting a lead related condition. For example, processor 80 may reconfigure sensing and/or therapy delivery to avoid use of channels with integrity issues. Additionally or alternatively, processor 80 may reconfigure sensing and/or therapy delivery parameters for channels with integrity issues. As one example, processor 80 may extend the blanking period of one or more sensing channels, e.g., amplifiers, of sensing module 86. As another example, processor 80 may increase a sensing threshold, e.g., a threshold used to detect cardiac events, such as depolarizations, following delivery of a therapeutic electrical signal, e.g., an ATP pulse. Extending a blanking period and/or increasing a threshold value may help prevent inappropriate detection of arrhythmias and/or other cardiac events.

As yet another example, in a channel used for pacing, processor 80 may extend the second phase of a biphasic pacing pulse, e.g., to greater than 16 milliseconds, in response to detecting a lead related condition in that channel. In some examples, processor 80 may extend the second phase of a biphasic pacing pulse to approximately 30 or more milliseconds. As yet another example, processor 80 may extend the second phase of a biphasic pacing pulse up to approximately 50 milliseconds. In this manner, the duration of the second phase of the pacing pulse may be increased relative to the duration of the second phase of biphasic pacing pulses delivered prior to detection of the lead related condition. Extending the second phase of the pacing pulse may allow the capacitive charge built up during the first phase of the pacing pulse to more fully dissipate. As an alternative, processor 80 may short the electrodes used to deliver a pacing pulse after delivering the pacing pulse to allow the charge to dissipate. Signal generator 84 and/or leads 18, 20, 22 may include one or more switches and/or multiplexers to facilitate shorting across the electrodes. If the pacing channel is also used to detect cardiac events, dissipating the charge may result in less noise and more accurate detection.

In some examples, processor 80 may provide an alert to a user, e.g., of programmer 24, regarding any detected lead related conditions via telemetry module 88. For example, programmer 24 may report the alert provided by processor 80 via user interface 104. Additionally or alternatively, IMD 16 may suggest a response to a lead related condition and/or receive user approval of a response via telemetry module 88. Alternatively, IMD 16 may provide an EGM or other sensed signal to an external device, e.g., programmer 24, via telemetry module 88 for identification of lead related conditions, and processor 100 of programmer 24 may automatically identify a lead related condition based on the sensed signal received from IMD 16.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In addition, processor 80 may transmit information regarding lead related conditions to programmer 24 via telemetry module 88. For example, processor 80 may provide an alert regarding any detected lead related conditions, suggest a response to a lead related condition, or provide an EGM or other sensed signal for identification of lead related conditions to programmer 24 via telemetry module 88. In some examples, processor 100 of programmer 24 may automatically identify a lead related condition based on the sensed signal received from IMD 16. For example, processor 100 may use any of the identification techniques described previously with respect to processor 80 of IMD 16. Processor 80 may also receive information regarding lead related conditions or responses to such conditions from programmer 24 via telemetry module 88.

In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician.

Figure 5:
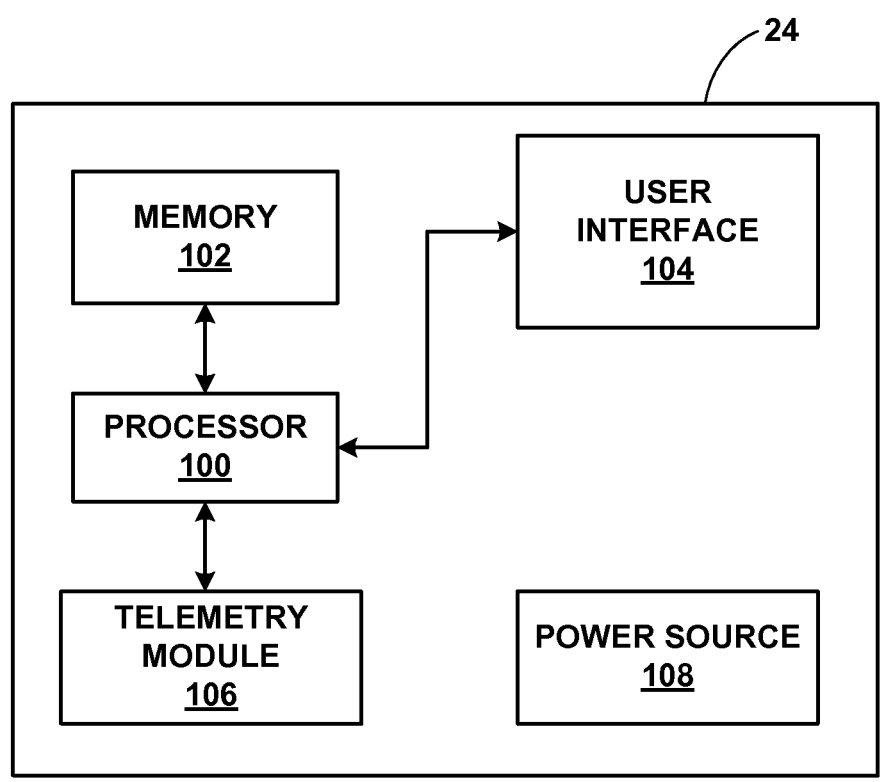
FIG. 5 is a functional block diagram illustrating an example configuration of an external programmer that facilitates user communication with the IMD.

FIG. 5 is functional block diagram illustrating an example configuration of programmer 24. As shown in FIG. 5, programmer 24 may include a processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

The user may also use programmer 24 to adjust or control the detection of lead related conditions performed by IMD 16. For example, the user may use programmer 24 to program the timing of electrical signals, the parameters of each electrical signal, or any other aspects of the integrity test. In this manner, the user may be able to finely tune the integrity test to the specific condition of patient 14. In some examples, the user uses programmer 24 to control the performance of an integrity test for detecting lead related conditions, e.g., in a clinic, hospital, or operating room setting, at the time of implant or during a follow-up visit.

In addition, the user may receive an alert from IMD 16 indicating a potential lead related condition via programmer 24. Programmer 24 may report the alert provided by IMD 16 via user interface 104. The user may respond to IMD 16 by suggesting a response to a detected lead related condition. Alternatively, IMD 16 may automatically suggest a response to a lead related condition. Such a response may also be displayed on user interface 104 of programmer 24. Programmer 24 may prompt the user to confirm the response.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 100 of programmer 24 and/or one or more processors of one or more networked computers may perform all or a portion of the techniques described herein with respect to processor 80 and IMD 16. For example, processor 100 or another processor may receive an EGM or other sensed signal for identification of lead related conditions.

Figure 6:
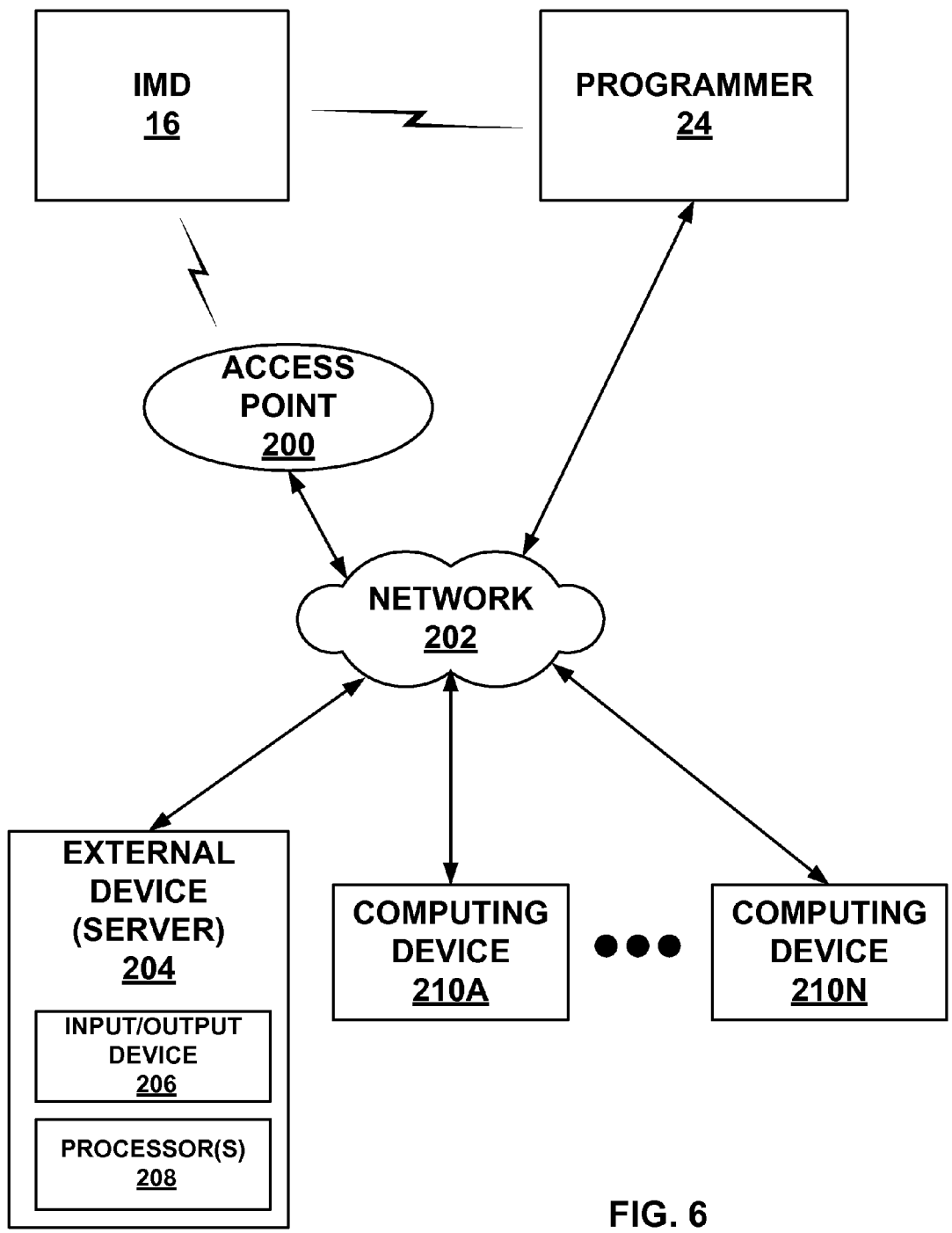
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 6, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other embodiments, access point 200 may be coupled to network 202 through different forms of connections, including wired or wireless connections. In some embodiments, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some embodiments, server 204 or computing devices 210 may control or perform any of the various functions or operations described herein, e.g., control performance of integrity tests by IMD 16.

In some cases, server 204 may be configured to provide a secure storage site for archival of sensing integrity information that has been collected from IMD 16 and/or programmer 24. Network 202 may comprise a local area network, wide area network, or global network, such as the Internet. In some cases, programmer 24 or server 204 may assemble sensing integrity information in web pages or other documents for viewing by and trained professionals, such as clinicians, via viewing terminals associated with computing devices 210. The system of FIG. 6 may be implemented, in some aspects, with general network technology and functionality similar to that provided by the Medtronic CareLink® Network developed by Medtronic, Inc., of Minneapolis, Minn.

Figure 7:
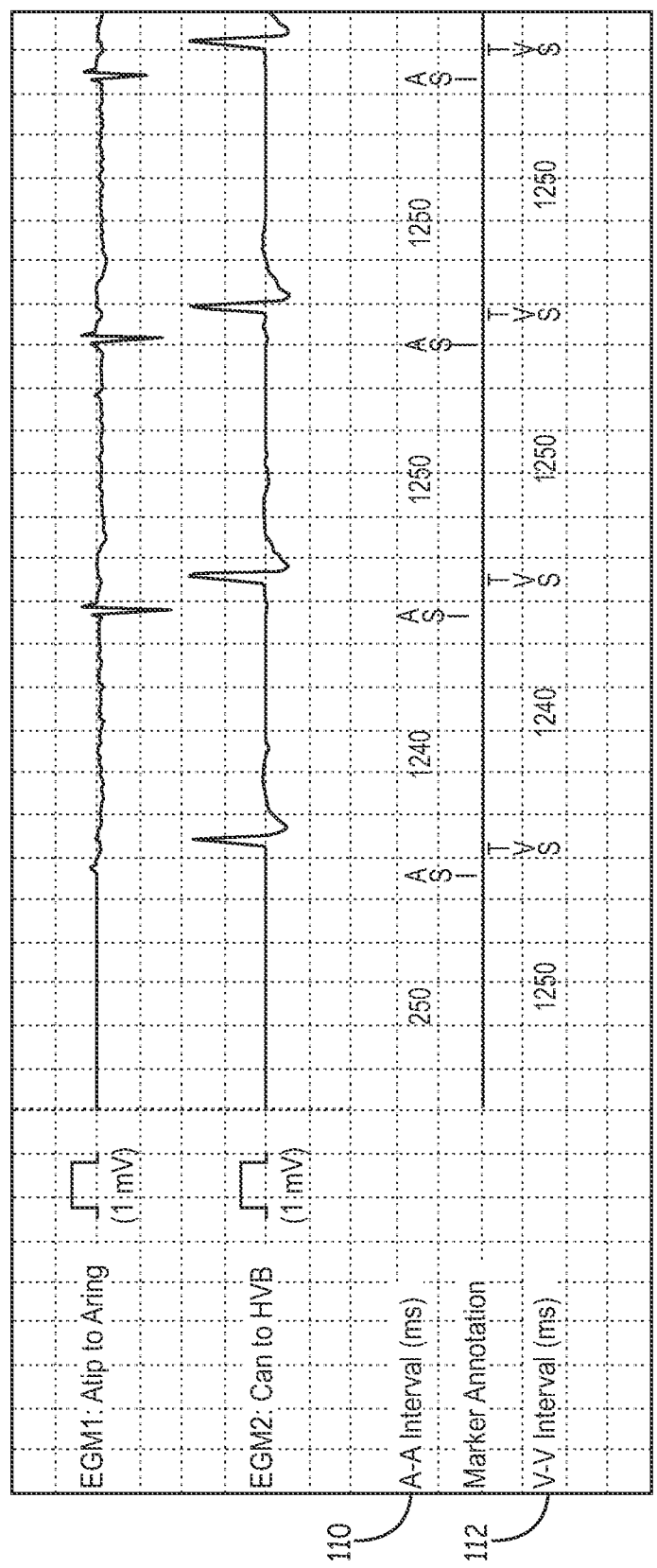
FIGS. 7-10 illustrate example electrogram (EGM) signals that may indicate lead related conditions.
Figure 8:
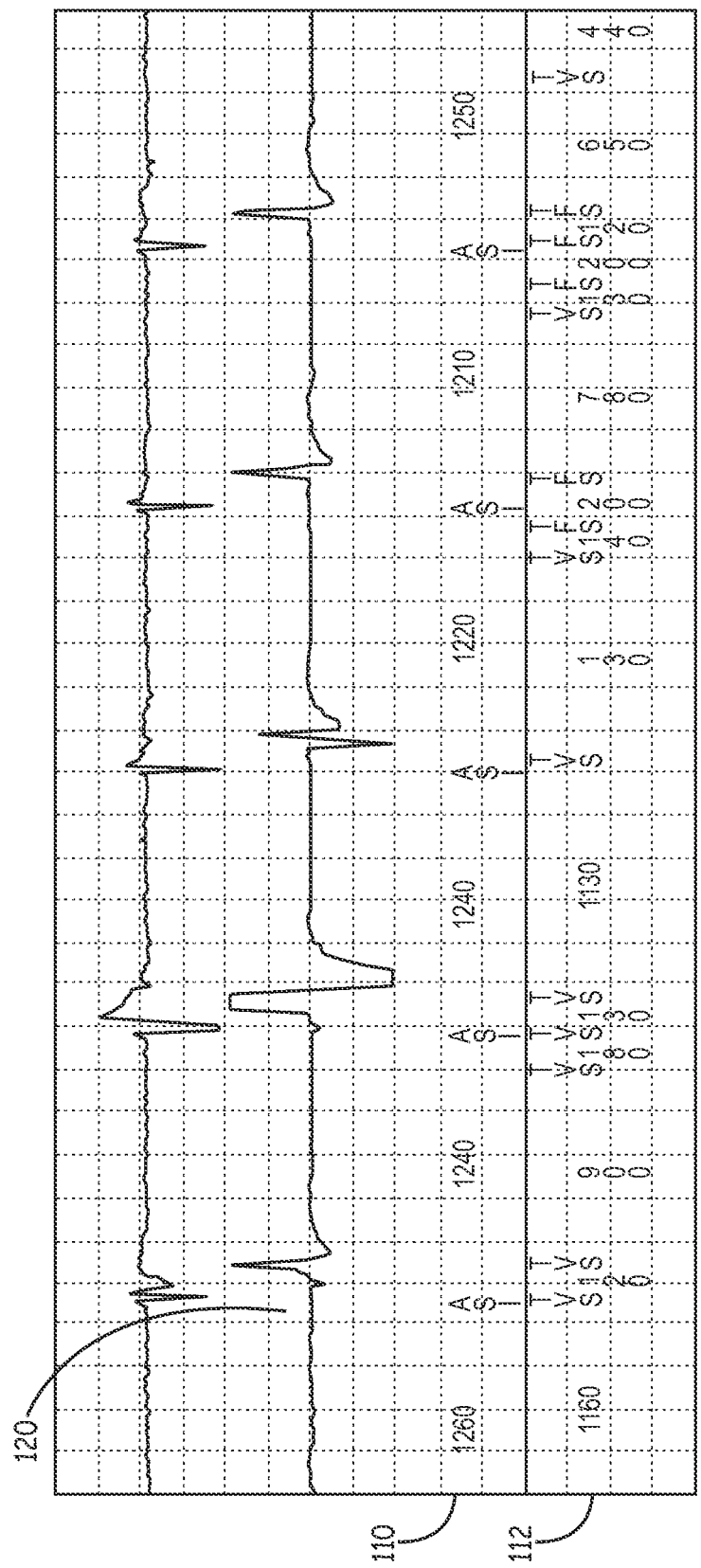

FIGS. 7-10 illustrate example EGM signals that may indicate lead related conditions. FIG. 7 illustrates an example normal EGM signal before any electrical signals are delivered. A-A intervals 110 and V-V intervals 112 are of consistent duration, and no atrial or ventricular contractions are inappropriately detected. FIG. 8 illustrates an example EGM signal after a sub-threshold electrical signal is delivered at time 120. Subsequent to the sub-threshold electrical signal, ventricular contractions are improperly detected due to signal noise resulting from a lead related condition. Consequently, detected V-V intervals 112 are of inconsistent duration.

Figure 9:
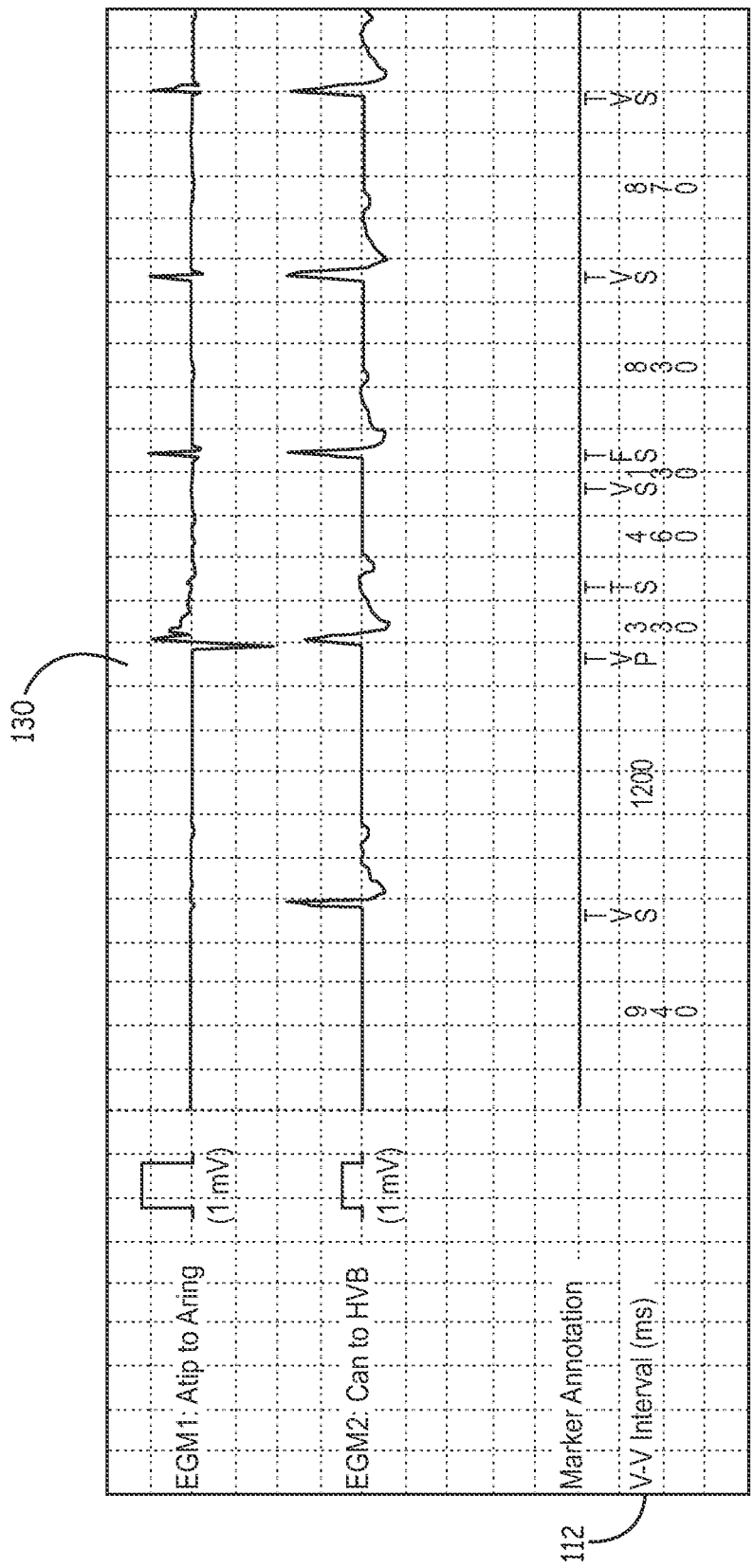
Figure 10:
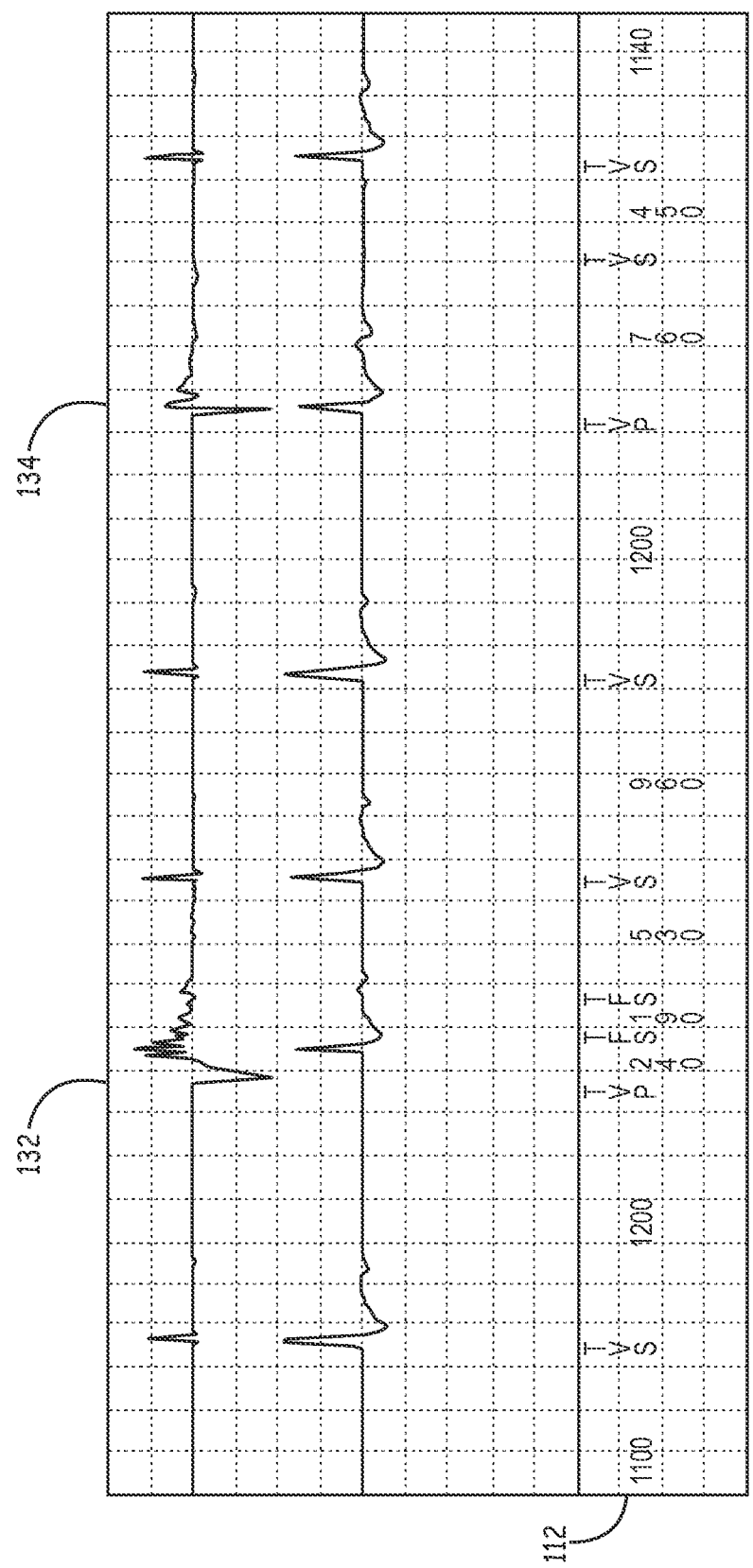

FIG. 9 illustrates an example EGM signal following a bradycardia pacing pulse at time 130. Similarly, FIG. 10 illustrates an example EGM signal following bradycardia pacing pulses at times 132 and 134. Subsequent to the bradycardia pacing pulses, ventricular contractions are improperly detected due to signal noise resulting from a lead related condition. Consequently, detected V-V intervals 112 are of inconsistent duration.

Figure 11:
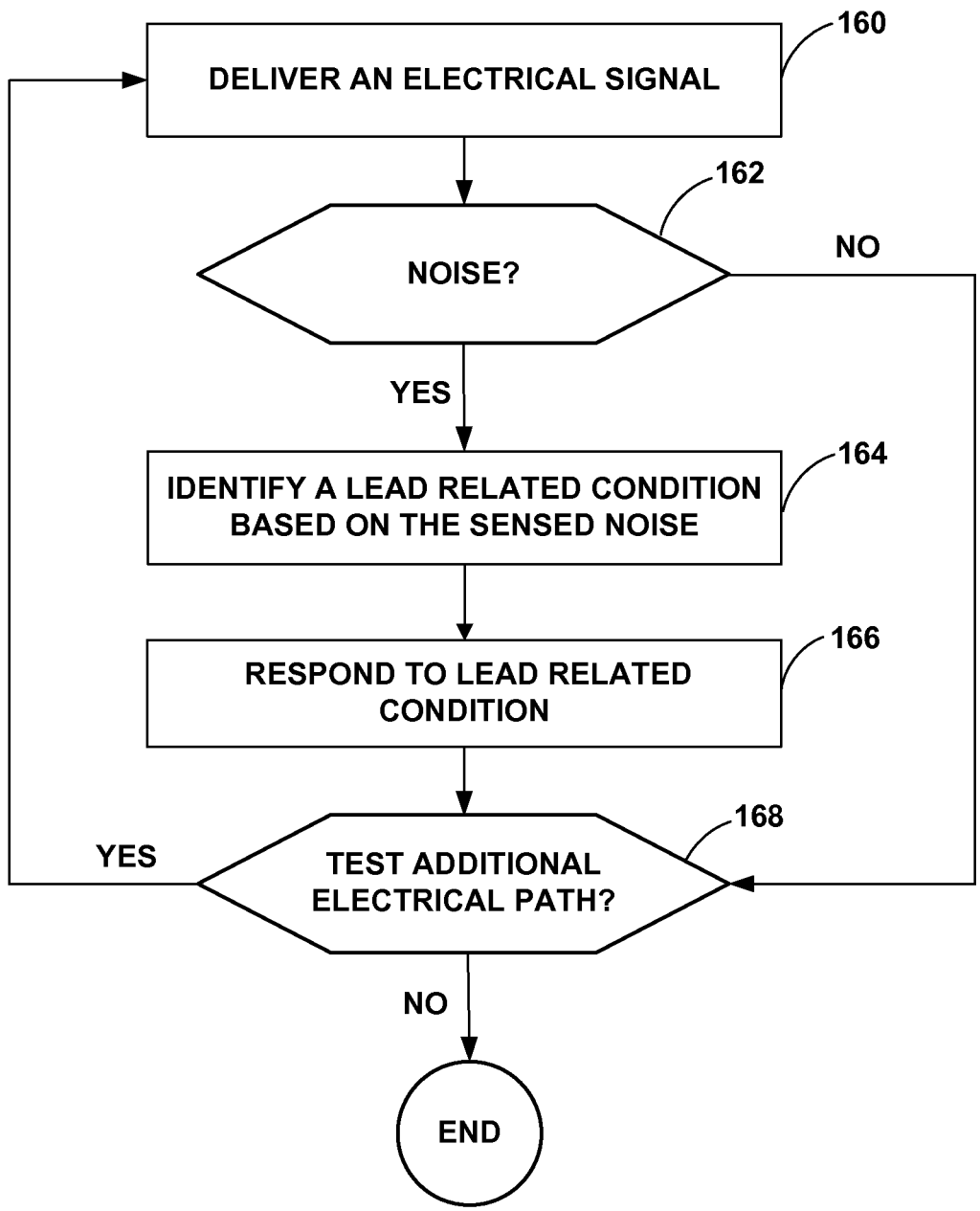
FIG. 11 is a flow diagram of an example method of identifying a lead related condition.

FIG. 11 is a flow diagram of an example method of identifying a lead related condition. The functionality described with respect to FIG. 11 as being provided a particular processor or device may, in other examples, be provided by any one or more of the processors or devices described herein.

Processor 80 may control signal generator 84 to deliver an electrical signal via an electrical path that includes a combination of the electrodes on one or more of leads 18, 20, 22. The electrical signal is configured to result in, reveal, or amplify electrical noise if a lead related condition, e.g., conductor or connector failure, or insulation breach, is present (160). If a lead related condition is present, the electrical signal may cause a build-up of capacitive charge, e.g., at the lead-tissue interface, at the location of the fracture point, and/or at another location along the electrical path. In addition, the lead related condition may be intermittent. As one example, an intermittent lead fracture or disconnection may fluctuate between a completed connection and a broken connection. The intermittent nature of the lead integrity issue may be detectable as noise indicative of a lead related condition on electrical path when the capacitive charge is present on the electrical path.

Processor 80 may control sensing module 86 to sense for electrical noise indicative of a lead related condition subsequent to the electrical signal (162). For example, sensing module 86 may sense an electrogram (EGM) signal using the electrode configuration used to deliver the electrical signal. Sensing module 86 may sense the EGM during a period having a predetermined length subsequent to the delivery of the electrical signal.

If processor 80 and/or sensing module 86 do not detect noise indicative of a lead related condition, processor 80 may determine whether to test the integrity of a different electrical path (168). If processor 80 and/or sensing module 86 detect noise indicative of a lead related condition, processor 80 may identify a lead related condition based on the sensed signal (164). For example, processor 80 may identify a lead related condition using thresholds and/or digital signal processing. In this manner, processor 80 may automatically identify a lead related condition based on the sensed signal.

Processor 80 may take one or more actions in response to detecting a lead related condition (166). For example, processor 80 may reconfigure sensing and/or therapy delivery to avoid use of channels with integrity issues. As another example, in a channel used for pacing, processor 80 may extend the second phase of a biphasic pacing pulse, e.g., to greater than 16 milliseconds. In some examples, processor 80 may extend the second phase of a biphasic pacing pulse to approximately 30 or more milliseconds. As yet another example, processor 80 may extend the second phase of a biphasic pacing pulse up to approximately 50 milliseconds. Extending the second phase of the pacing pulse may allow the capacitive charge built up during the first phase of the pacing pulse to more fully dissipate. As an alternative, processor 80 may short across the electrode after delivering a pacing pulse to allow the charge to dissipate. Signal generator 84 and/or leads 18, 20, 22 may include one or more switches and/or multiplexers to facilitate shorting across the electrode. If the pacing channel is also used to detect cardiac events, dissipating the charge may result in less noise and more accurate detection.

Processor 80 may determine whether to test the integrity of an additional electrical path (168). For example, signal generator 84 may deliver an electrical signal to a different combination of the electrodes on one or more of leads 18, 20, 22 to test the integrity of another electrical path. As one example, processor 80 may test a plurality of electrical paths according to a schedule stored within memory 82. The schedule may include a plurality of electrical paths that IMD 16 uses for sensing and/or therapy delivery. As another example, if an integrity issue is detected along one electrical path, processor 80 may test alternate electrode configurations to identify which conductor is experiencing an integrity issue. For example, if an integrity issue is detected when electrodes 40 and 42 are activated, processor 80 may test electrodes 40 and 42 independently, e.g., by separately testing each of 40 and 42 in combination with housing electrode 58, to determine which one of electrodes 40 and 42 is causing the issue. In some examples, processor 80 may not may take one or more actions in response to detecting a lead related condition (166) until processor 80 identifies which conductor is experiencing an integrity issue, e.g., by testing the electrodes of an electrical path with an identified lead related condition independently.

FIGS. 12A-15B illustrate example EGM signals collected from patients that experienced lead fractures. EGM signals indicating noise related to lead fractures from 44 patients were collected and analyzed. All of the lead fractures were confirmed by analysis of returned, explanted leads.

EGMs were collected and analyzed if a true-bipolar, i.e., tip-ring, EGM was recorded and included at least three sensed and at least three paced true ventricular beats. EGMs were censored at the first shock. Up to five EGMs were analyzed per patient.

Various patterns of noise and oversensing indicative of lead related conditions were observed. Pacing-induced oversensing was defined as oversensing caused by high-frequency, nonphysiological signals that either occurred transiently after a ventricular paced beat (e.g., VP) but not after ventricular sensed beats (e.g., VS), or was absent after ventricular sensed beats (e.g., VS) but persisted longer than one cardiac cycle after a ventricular paced beat (e.g., VP). Noise and oversensing that occurred only after ventricular sensed beats fulfilled the reverse criteria.

Figure 12A:
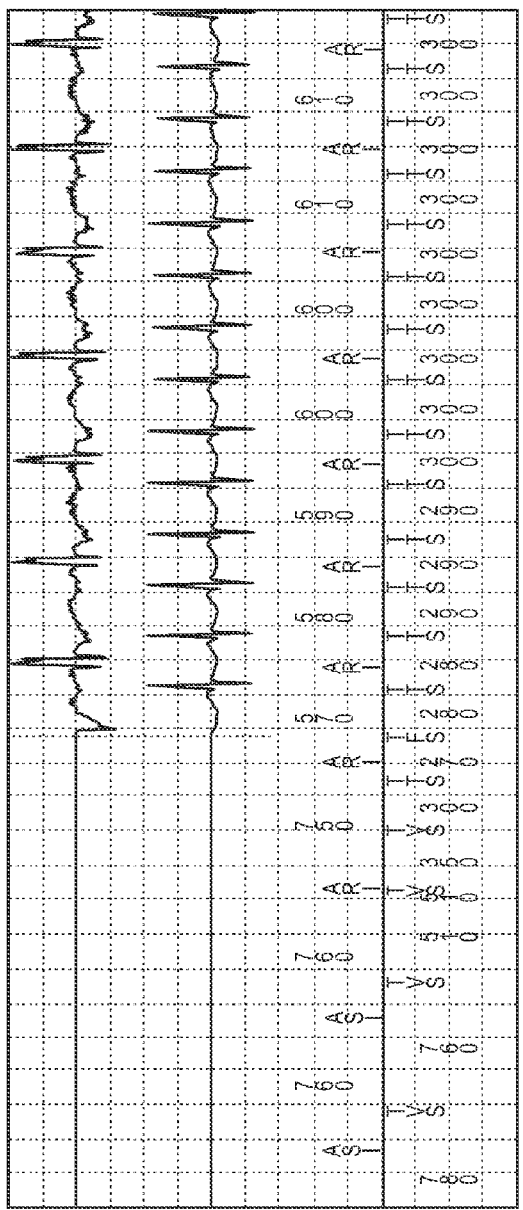
FIGS. 12-15B illustrate example electrogram (EGM) signals collected from patients that experienced lead fractures.
Figure 12B:
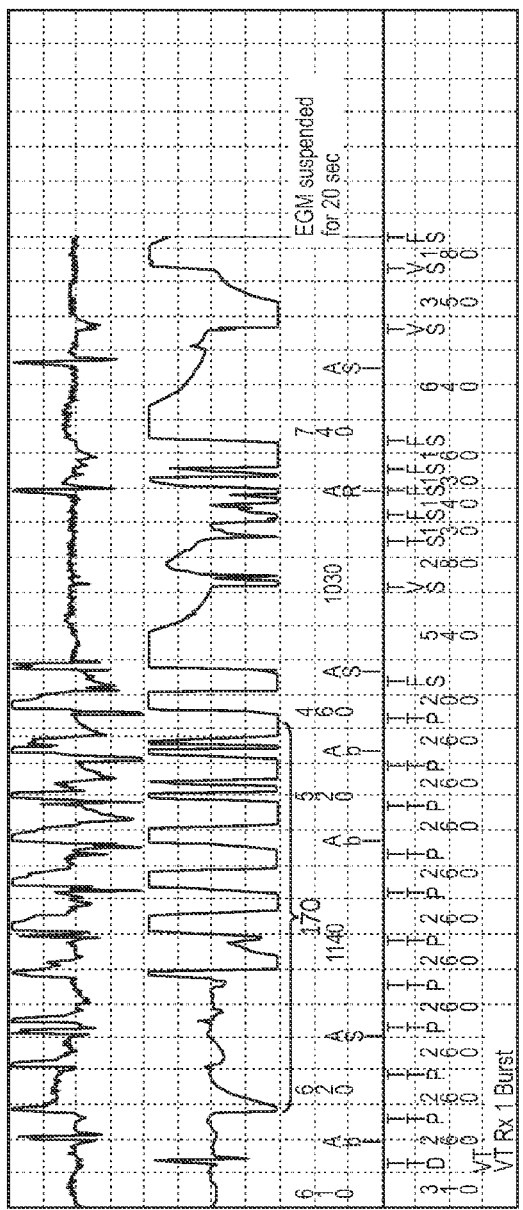

An example of persistent noise following delivery of anti-tachycardia pacing pulses (TP) at time 170 is illustrated in FIGS. 12A and 12B. In particular, FIG. 12A illustrates an absence of oversensing during a series of ventricular sensed beats that met a ventricular tachycardia criterion (TS). Noise is evident following delivery of ventricular anti-tachycardia pacing pulses (TP) during time 170, as illustrated in FIG. 12B. Persistent oversensing following the anti-tachycardia pacing pulses (TP) is illustrated by the ventricular sensed beats meeting the tachycardia (TS) and fibrillation (FS) criteria during the cardiac cycle following the anti-tachycardia pacing pulses (TP).

Figure 13A:
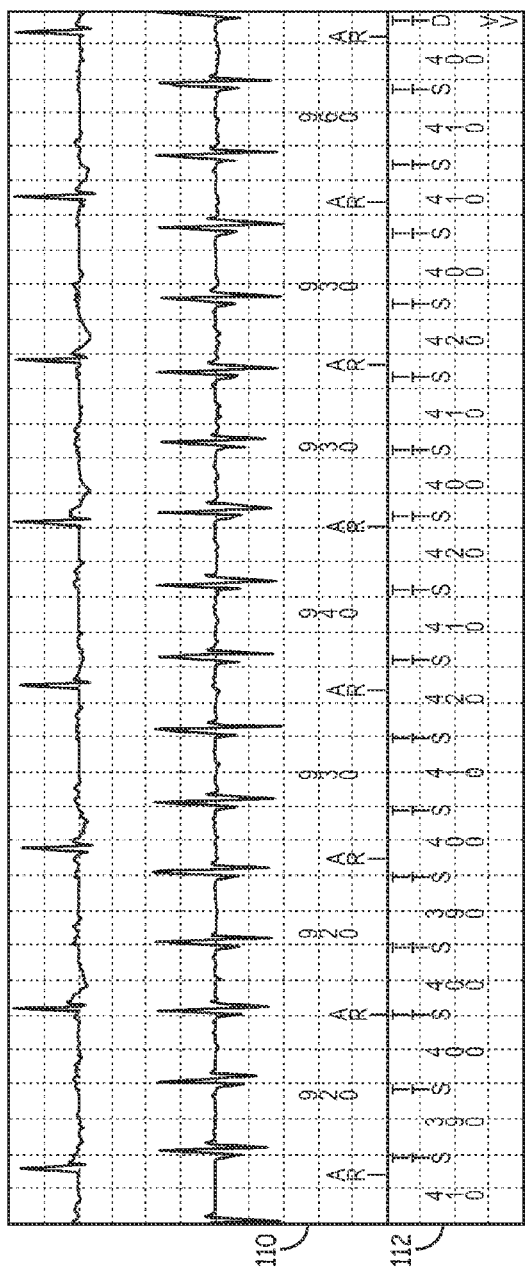
Figure 13B:
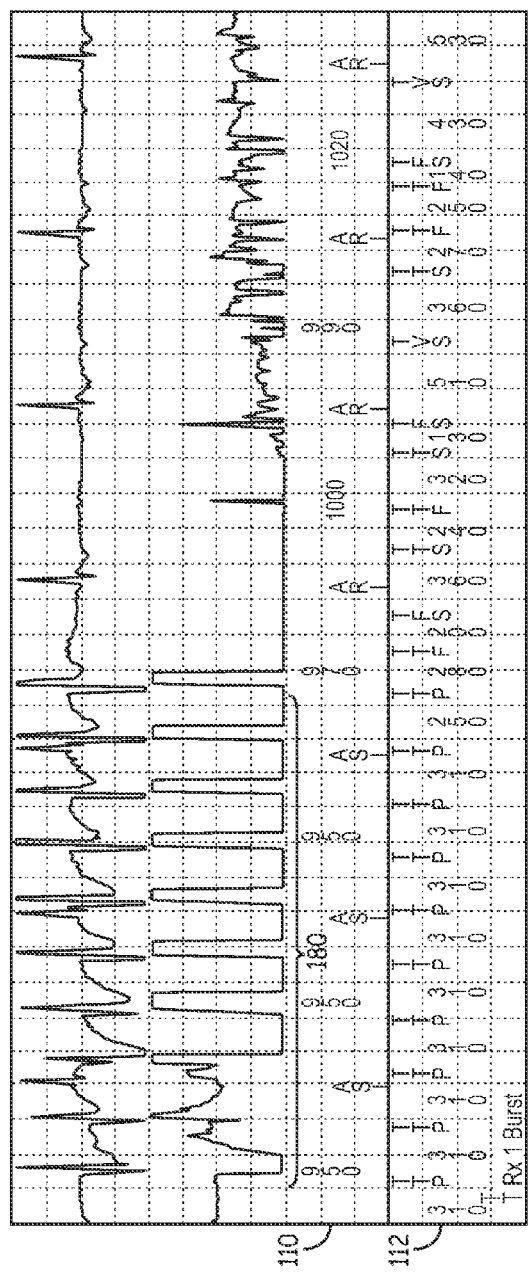

FIGS. 13A and 13B illustrate an example of transient oversensing. FIG. 13A illustrates an absence of noise during a series of ventricular sensed beats that met a ventricular tachycardia criterion (TS). Noise is evident following delivery of ventricular anti-tachycardia pacing during time 180, as illustrated in FIG. 13B. Transient oversensing following the anti-tachycardia pacing pulses (TP) is illustrated by the ventricular sensed beats meeting the tachycardia (TS) and fibrillation (FS) criteria during the cardiac cycle following the anti-tachycardia pacing pulses (TP).

Figure 14:

Another example of transient noise is illustrated in FIG. 14 following delivery of a ventricular bradycardia pacing pulse (VP) at time 190. Transient oversensing following the pacing pulse is evidenced by the ventricular sensed beats meeting the fibrillation (FS) criterion during the cardiac cycle following the ventricular bradycardia pacing pulse (VP).

Figure 15A:
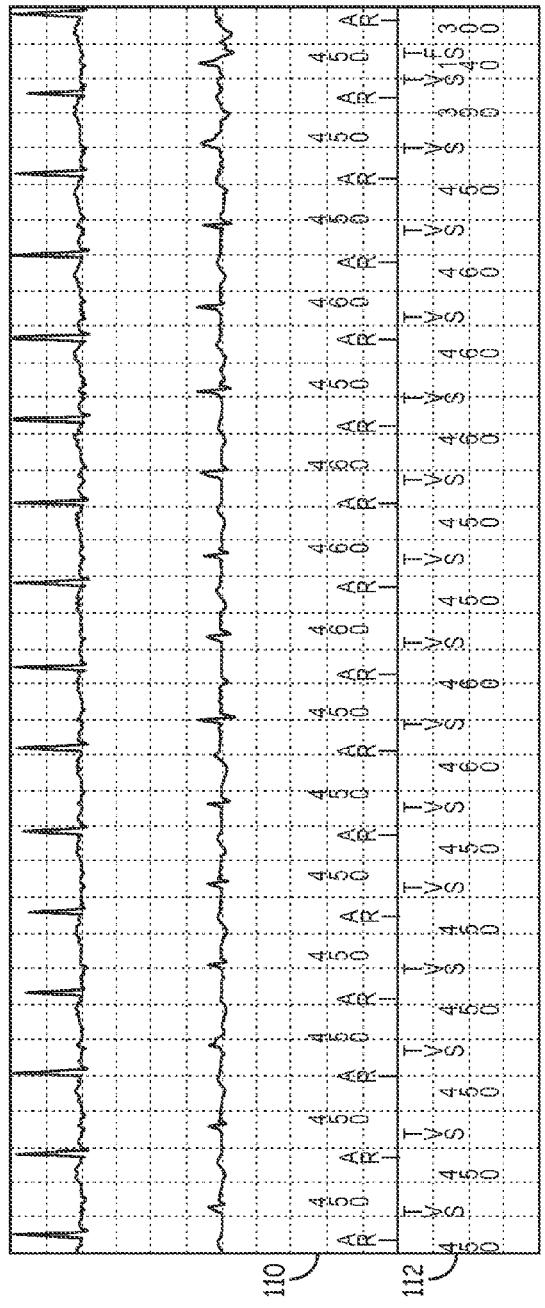
Figure 15B:
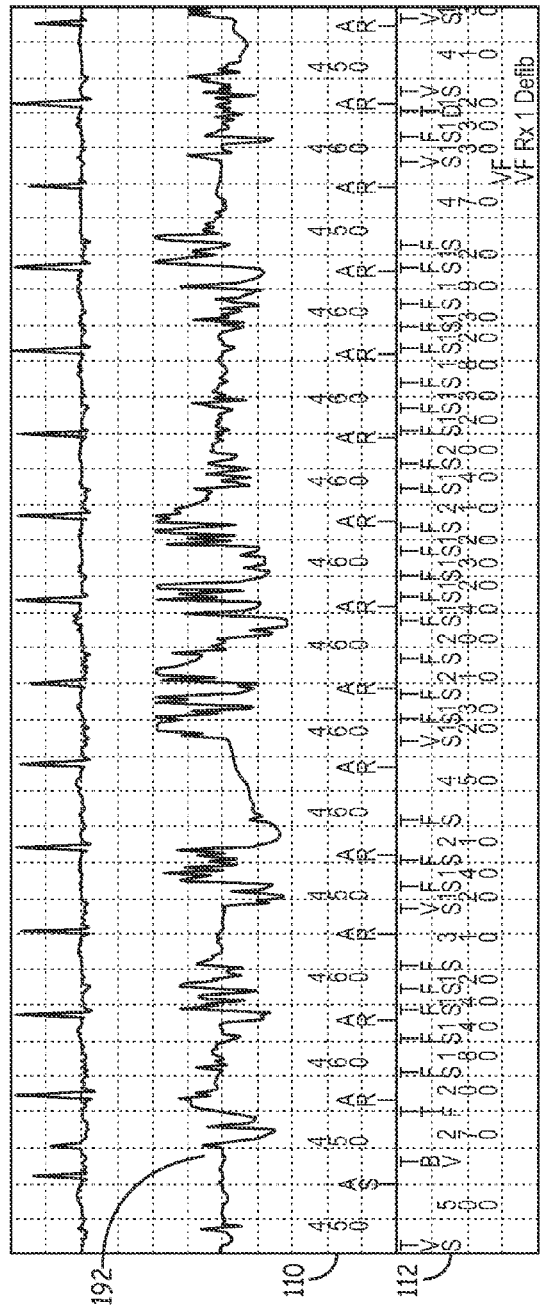

FIGS. 15A and 15B illustrate another example of persistent noise following delivery of biventricular pacing pulses (BV) at time 192. Persistent oversensing lasting greater than one cardiac cycle after the pacing pulses is evidenced by the sensed ventricular beats meeting the fibrillation criterion (FS) following the pacing pulses and more than one cardiac cycle after the pacing pulses.

Overall 153 EGMs in 44 patients included at least three ventricular pace beats and at least three ventricular sensed beats. Oversensing was not related to ventricular pacing or ventricular sensing in 35 pts (80%). No patient had oversensing only after ventricular sensing. Pacing-induced oversensing occurred in 9 patients (20%, P<0.001). 2 of the 9 patients that experienced pacing-induced oversensing did not receive bradycardia pacing therapy. In these 2 patients, pacing-induced oversensing occurred only after antitachycardia pacing. Pacing-induced oversensing occurred in 14% of all EGMs analyzed (22/153). Of the 44 patients studied fractures occurred in the cable conductor to the ring electrode in 22 patients and in the coil conductor to the tip electrode in 22 patients. Pacing-induced oversensing occurred in 36% of cable fractures (8/22) versus 5% of coil fractures (1/22), p=0.02.

Detecting noise indicative of a lead related condition subsequent to the delivery of an electrical signal may provide insight into the origin of lead-noise signals. Since many patients with implantable cardiac devices, such as implantable cardioverter defibrillators, do not receive ventricular pacing or other electrical signals that may result in, reveal, or amplify, noise indicative of a lead related condition for therapeutic reasons, delivery of such signals may be performed to provoke noise indicative of lead related conditions in these patients, e.g., patient who are in ventricular sinus rhythm.

FIGS. 16A and 16B illustrate example electrogram (EGM) signals that may indicate lead related conditions. In particular, FIGS. 16A and 16B illustrate pacing-exacerbated oversensing. Pacing-exacerbated oversensing results in a marked increase in amplitude and duration of noise resulting in a marked increase in oversensing after ventricular pacing. Examples of pacing exacerbated noise are illustrated in FIGS. 16A and 16B, in which the amplitude and/or duration of noise increases subsequent to delivery of biventricular pacing pulses, e.g., at times 200A, 200B, and 200C, as examples. Oversensing evidenced by fibrillation senses (FS) is present after ventricular sensed beats (VS), but increases following the delivery of the pacing pulses.

Various examples have been described. These and other examples are within the scope of the following claims. For example, although detection of lead related conditions is directed herein toward cardiac therapy, this disclosure may also be applicable to other therapies in which detection of lead related conditions may be appropriate. These therapies may include spinal cord stimulation, deep brain stimulation, pelvic floor stimulation, gastric stimulation, occipital stimulation, functional electrical stimulation, and any other stimulation therapy utilizing electrode sensing and/or stimulation methods. Furthermore, although described herein as implemented by an IMD and system including an IMD, in other examples, the techniques described herein may be implemented in an external medical device. An external medical device may be coupled to leads during implant, and may perform a lead integrity test as described herein to detect any lead related conditions of the recently implanted leads.

In addition, it should be noted that therapy system 10 may not be limited to treatment of a human patient. In alternative examples, therapy system 10 may be implemented in non-human patients, e.g., primates, canines, equines, pigs, and felines. These other animals may undergo clinical or research therapies that my benefit from the subject matter of this disclosure.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The invention claimed is:

1. A method comprising:
   delivering an electrical signal between two or more implanted electrodes and via an implanted medical lead that carries at least one of the two or more implanted electrodes;
   sensing an electrogram signal with the two or more implanted electrodes and via the implanted medical lead during a period having a predetermined length subsequent to delivery of the electrical signal;
   detecting, based on the sensed electrogram signal, noise induced by the delivered electrical signal and indicative of a lead related condition of the implanted medical lead within the electrogram signal during the period having the predetermined length subsequent to the delivery of the electrical signal; and
   identifying, by a processor, the lead related condition of the implanted medical lead in response to the detection of the noise indicative of the lead related condition within the electrogram signal during the period having the predetermined length subsequent to the delivery of the electrical signal.

2. The method of claim 1, wherein the electrical signal comprises a pacing stimulus configured to capture cardiac tissue.

3. The method of claim 1, wherein the electrical signal comprises a non-therapeutic electrical signal configured to avoid tissue capture.

4. The method of claim 3, wherein the non-therapeutic electrical signal is delivered during a refractory period of a heart.

5. The method of claim 3, wherein the non-therapeutic electrical signal comprises a subthreshold signal.

6. The method of claim 1, wherein the electrical signal comprises both a therapeutic electrical signal configured to capture tissue and at least one subsequent non-therapeutic electrical signal configured to avoid tissue capture.

7. The method of claim 1, wherein determining whether noise induced by the delivered electrical signal and indicative of the lead related condition is present within the electrogram signal comprises utilizing at least one of a threshold comparison or digital signal processing to determine whether noise induced by the delivered electrical signal and indicative of the lead related condition is present within the electrogram signal.

8. The method of claim 1, wherein the predetermined length subsequent to the delivery of the electrical signal is approximately two seconds.

9. The method of claim 1, further comprising:
   increasing a duration of a second phase of a biphasic therapeutic pulse configured to capture tissue in response to identifying the lead related condition; and
   delivering the biphasic therapeutic pulse between the two or more implanted electrodes and via the implanted medical lead.

10. The method of claim 1, further comprising:
    delivering a therapeutic electrical signal configured to capture tissue between the two or more implanted electrodes and via the implanted medical lead subsequent to identifying the lead related condition; and
    based on identifying the lead related condition, shorting an electrical path of the two or more implanted electrodes and the implanted medical lead subsequent to delivering the therapeutic electrical signal.

11. The method of claim 1, further comprising extending a blanking period of a sensing channel in response to identifying the lead related condition.

12. The method of claim 1, further comprising increasing a threshold used for sensing a cardiac event in response to identifying the lead related condition.

13. The method of claim 1, further comprising identifying, based on the sensed electrogram signal, the lead related condition.

14. A system comprising:
    a signal generator configured to deliver an electrical signal between two or more implanted electrodes and via an implanted medical lead that carries at least one of the two or more implanted electrodes; and
    a sensing module configured to:
      sense an electrogram signal with the two or more implanted electrodes and via the implanted medical lead during a period having a predetermined length subsequent to delivery of the electrical signal; and
      detecting, based on the sensed electrogram signal, noise induced by the delivered electrical signal and indicative of a lead related condition of the implanted medical lead within the electrogram signal during the period having the predetermined length subsequent to the delivery of the electrical signal; and
    a processor configured to identify the lead related condition of the implanted medical lead in response to the detection of the noise indicative of the lead related condition within the electrogram signal during the period having the predetermined length subsequent to the delivery of the electrical signal.

15. The system of claim 14, wherein the electrical signal comprises a pacing stimulus configured to capture cardiac tissue.

16. The system of claim 14, wherein the electrical signal comprises a non-therapeutic electrical signal configured to avoid tissue capture.

17. The system of claim 16, wherein the signal generator is configured to deliver the non-therapeutic electrical signal during a refractory period of a heart.

18. The system of claim 16, wherein the non-therapeutic electrical signal comprises a subthreshold signal.

19. The system of claim 14, wherein the signal generator is configured to deliver both a therapeutic electrical signal configured to capture tissue and at least one subsequent non-therapeutic electrical signal configured to avoid tissue capture.

20. The system of claim 14, wherein the sensing module is configured to determine whether noise induced by the delivered electrical signal and indicative of the lead related condition is present within the electrogram signal using at least one of a threshold comparison or digital signal processing.

21. The system of claim 14, wherein the predetermined length subsequent to the delivery of the electrical signal is approximately two seconds.

22. The system of claim 14, wherein the processor is configured to increase a duration of a second phase of a biphasic therapeutic pulse configured to capture tissue in response to identifying the lead related condition, and wherein the signal generator is configured to deliver the biphasic therapeutic pulse between the two or more implanted electrodes and via the implanted medical lead.

23. The system of claim 14, wherein the signal generator is configured to deliver a therapeutic electrical signal configured to capture tissue between the two or more implanted electrodes and via the implanted medical lead subsequent to identifying the lead related condition, and wherein the processor is configured to, based on identifying the lead related condition, short an electrical path of the two or more implanted electrodes and the implanted medical lead subsequent to delivering the therapeutic electrical signal.

24. The system of claim 14, wherein the processor is configured to extend a blanking period of a sensing channel of the sensing module in response to identifying the lead related condition.

25. The system of claim 14, wherein the processor is configured to, in response to identifying the lead related condition, increase a threshold used by the sensing module to sense a cardiac event.

26. The system of claim 14, wherein the electrical signal comprises at least one of a maximum amplitude or a maximum pulse width provided by the signal generator.

27. The system of claim 14, further comprising an implantable medical device comprising the signal generator and the sensing module.

28. The system of claim 27, wherein the implantable medical device comprises the processor.

29. The system of claim 27, wherein the implantable medical device comprises at least one of a pacemaker, cardioverter, or defibrillator.

30. A system comprising:
  means for delivering an electrical signal between two or more implanted electrodes and via an implanted medical lead that carries at least one of the two or more implanted electrodes;
  means for sensing an electrogram signal with the two or more implanted electrodes and via the implanted medical lead during a period having a predetermined length subsequent to delivery of the electrical signal;
  means for detecting, based on the sensed electrogram signal, noise induced by the delivered electrical signal and indicative of a lead related condition of the implanted medical lead within the electrogram signal during the period having the predetermined length subsequent to the delivery of the electrical signal; and
  means for identifying the lead related condition of the implanted medical lead in response to the detection of the noise indicative of the lead related condition within the electrogram signal during the period having the predetermined length subsequent to the delivery of the electrical signal.

31. The system of claim 30, wherein the electrical signal comprises a pacing stimulus configured to capture cardiac tissue.

32. The system of claim 30, wherein the electrical signal comprises a non-therapeutic electrical signal configured to avoid tissue capture.

33. A non-transitory computer-readable storage medium comprising instructions for causing a programmable processor to:
  deliver an electrical signal between two or more implanted electrodes and via an implanted medical lead that carries at least one of the two or more implanted electrodes;
  sense an electrogram signal with the two or more implanted electrodes and the implanted medical lead during a period having a predetermined length subsequent to delivery of the electrical signal;
  detect, based on the sensed electrogram signal, noise induced by the delivered electrical signal and indicative of a lead related condition of the implanted medical lead within the electrogram signal during the period having the predetermined length subsequent to the delivery of the electrical signal; and
  identify the lead related condition of the implanted medical lead in response to the detection of the noise indicative of the lead related condition within the electrogram signal during the period having the predetermined length subsequent to the delivery of the electrical signal.

34. A method comprising:
  delivering an electrical signal via an electrical path that includes a medical lead;
  detecting noise indicative of a lead related condition on the electrical path within during a period having a predetermined length subsequent to the delivery of the electrical signal;
  identifying, by a processor, a lead related condition in response to the detection of the noise indicative of the lead related condition;
  delivering a therapeutic electrical signal configured to capture tissue via the electrical path subsequent to identifying the lead related condition; and
  based on identifying the lead related condition, shorting the electrical path subsequent to delivering the therapeutic electrical signal.

* * * * *